United States Patent
Weststrate et al.

(10) Patent No.: US 8,043,261 B2
(45) Date of Patent: Oct. 25, 2011

(54) METHOD FOR PERCUTANEOUSLY IMPLANTING A MEDICAL CATHETER AND MEDICAL CATHETER IMPLANTING ASSEMBLY

(75) Inventors: Patrice A. Weststrate, Norwood, MA (US); Boyd A. Colvin, Indianapolis, IN (US); Changqing Li, Bloomington, IN (US); Mark L. Adams, Sandy, UT (US); Donald C. Hovey, Sherborn, MA (US); Laurence D. Brenner, Boylston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/640,708

(22) Filed: Dec. 17, 2009

(65) Prior Publication Data

US 2010/0094212 A1    Apr. 15, 2010

Related U.S. Application Data

(63) Continuation of application No. 10/846,833, filed on May 14, 2004, now Pat. No. 7,654,980.

(51) Int. Cl.
*A61M 29/00* (2006.01)
*A61M 5/32* (2006.01)

(52) U.S. Cl. .................. 604/104; 604/174; 606/192

(58) Field of Classification Search .............. 604/104, 604/174, 175
See application file for complete search history.

(56) References Cited

U.S. PATENT DOCUMENTS

| | | | |
|---|---|---|---|
| 4,705,040 A | 11/1987 | Mueller et al. | |
| 4,861,334 A | 8/1989 | Nawaz | |
| 4,900,306 A | 2/1990 | Quinn et al. | |
| 5,112,310 A * | 5/1992 | Grobe | 604/175 |
| 5,167,627 A | 12/1992 | Clegg et al. | |
| 5,234,454 A * | 8/1993 | Bangs | 606/191 |
| 5,318,543 A * | 6/1994 | Ross et al. | 604/170.01 |
| 5,341,823 A | 8/1994 | Manosalva et al. | |
| 5,391,159 A * | 2/1995 | Hirsch et al. | 604/268 |
| 5,628,753 A * | 5/1997 | Cracauer et al. | 606/108 |
| 6,030,364 A * | 2/2000 | Durgin et al. | 604/164.01 |
| 6,402,722 B1 * | 6/2002 | Snow et al. | 604/164.05 |
| 6,488,691 B1 * | 12/2002 | Carroll et al. | 606/148 |
| 7,815,629 B2 * | 10/2010 | Klein et al. | 604/540 |
| 2002/0002361 A1 | 1/2002 | Fanelli et al. | |

(Continued)

FOREIGN PATENT DOCUMENTS

EP           0745353 A1    12/1996

*Primary Examiner* — Nicholas D Lucchesi
*Assistant Examiner* — Ian Holloway
(74) *Attorney, Agent, or Firm* — Kenyon & Kenyon LLP

(57) ABSTRACT

A method for percutaneously implanting a medical catheter, such as a gastrostomy feeding tube, and a medical catheter implanting assembly. In one embodiment, the implanting assembly includes a gastrostomy feeding tube, an inner sheath and an outer sheath. The feeding tube has an internal bolster integrally formed at its distal end. The inner sheath includes a bore extending distally from its proximal end to a point prior to its distal end and a transverse window communicating with the bore. The outer sheath includes a proximal end, a distal end and a longitudinal bore. The outer sheath is inserted over the inner sheath, and the feeding tube is inserted into the inner sheath, with the internal bolster being folded and tucked into the window and retained therein by the outer sheath. Movement of the outer sheath relative to the inner sheath to expose the window allows the bolster to decompress.

20 Claims, 17 Drawing Sheets

U.S. PATENT DOCUMENTS

| | | | |
|---|---|---|---|
| 2003/0139703 A1* | 7/2003 | Burkett et al. | 604/96.01 |
| 2004/0059293 A1 | 3/2004 | Chu et al. | |
| 2005/0256455 A1* | 11/2005 | Weststrate et al. | 604/104 |
| 2007/0255222 A1* | 11/2007 | Li et al. | 604/174 |
| 2008/0119793 A1* | 5/2008 | Adams et al. | 604/174 |
| 2008/0275484 A1* | 11/2008 | Gertner | 606/192 |

* cited by examiner

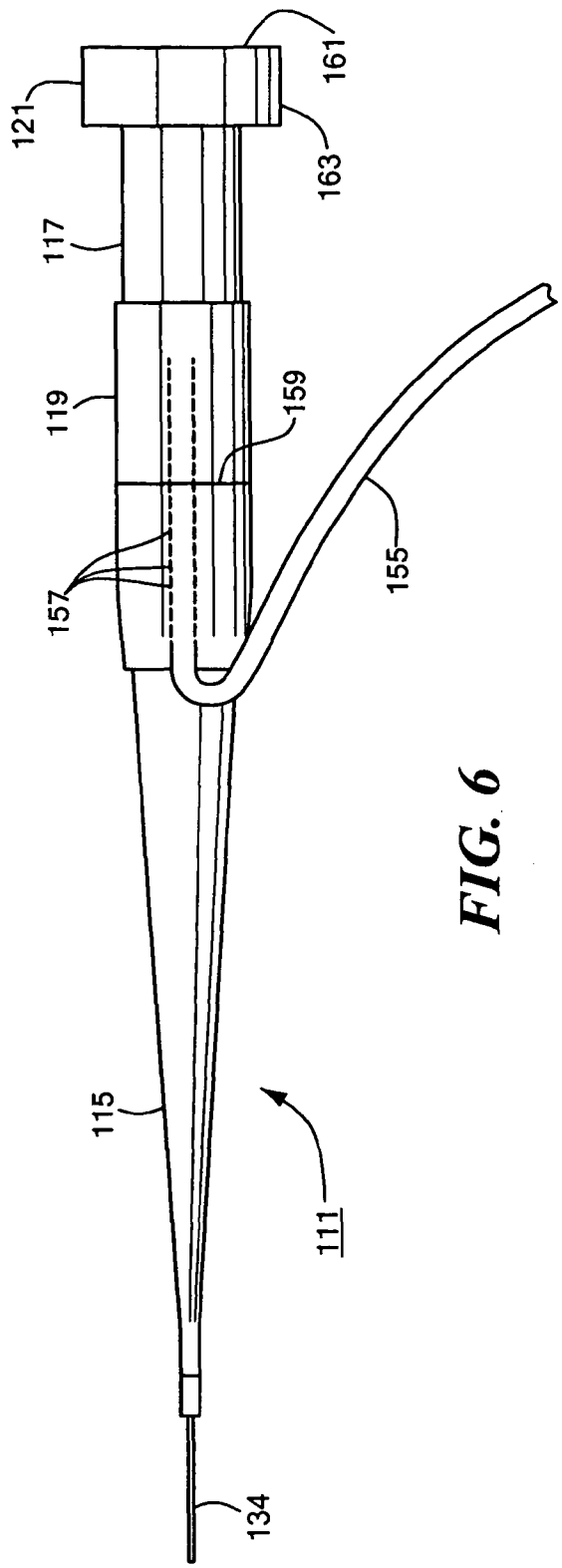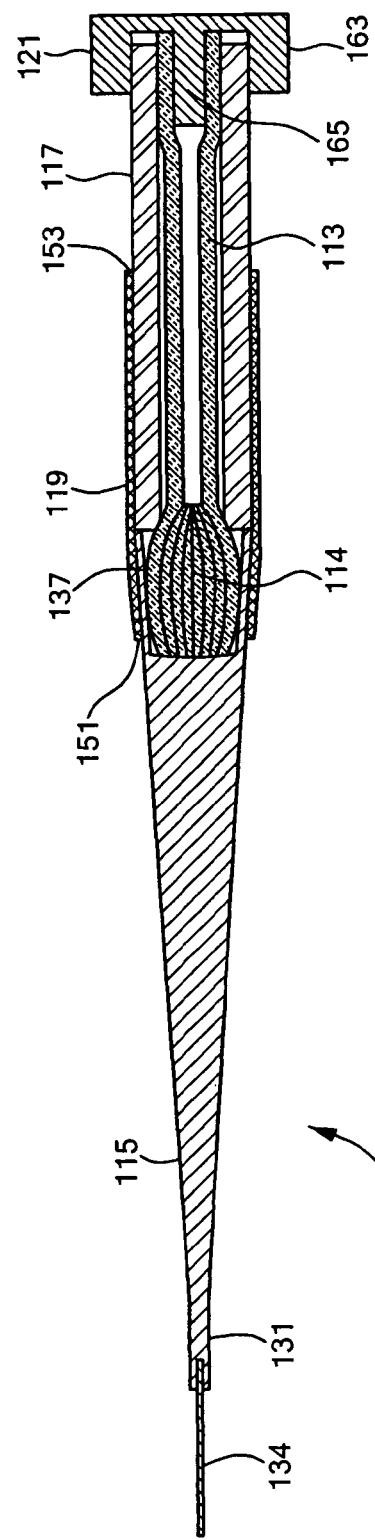
FIG. 6
FIG. 7

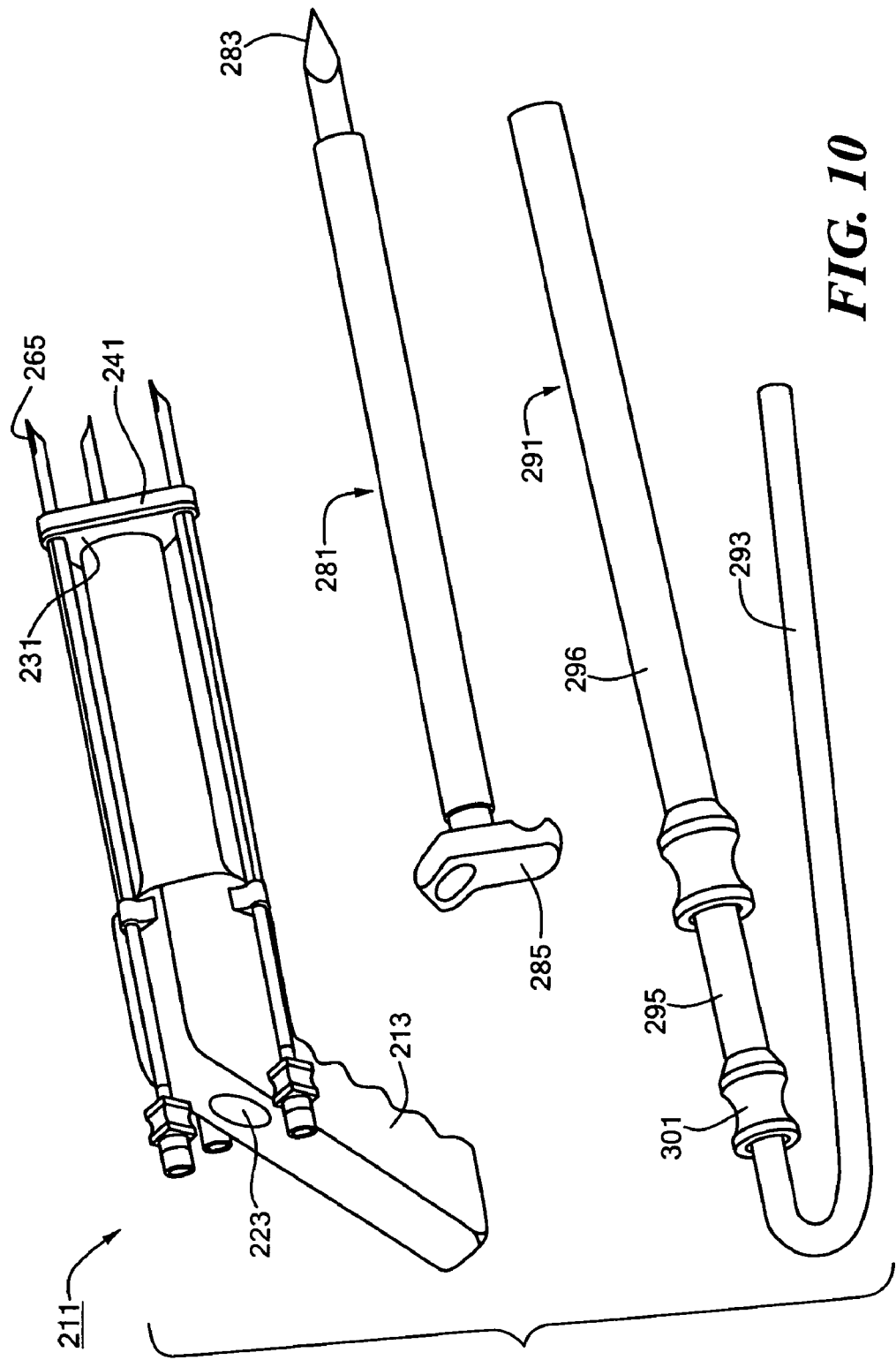

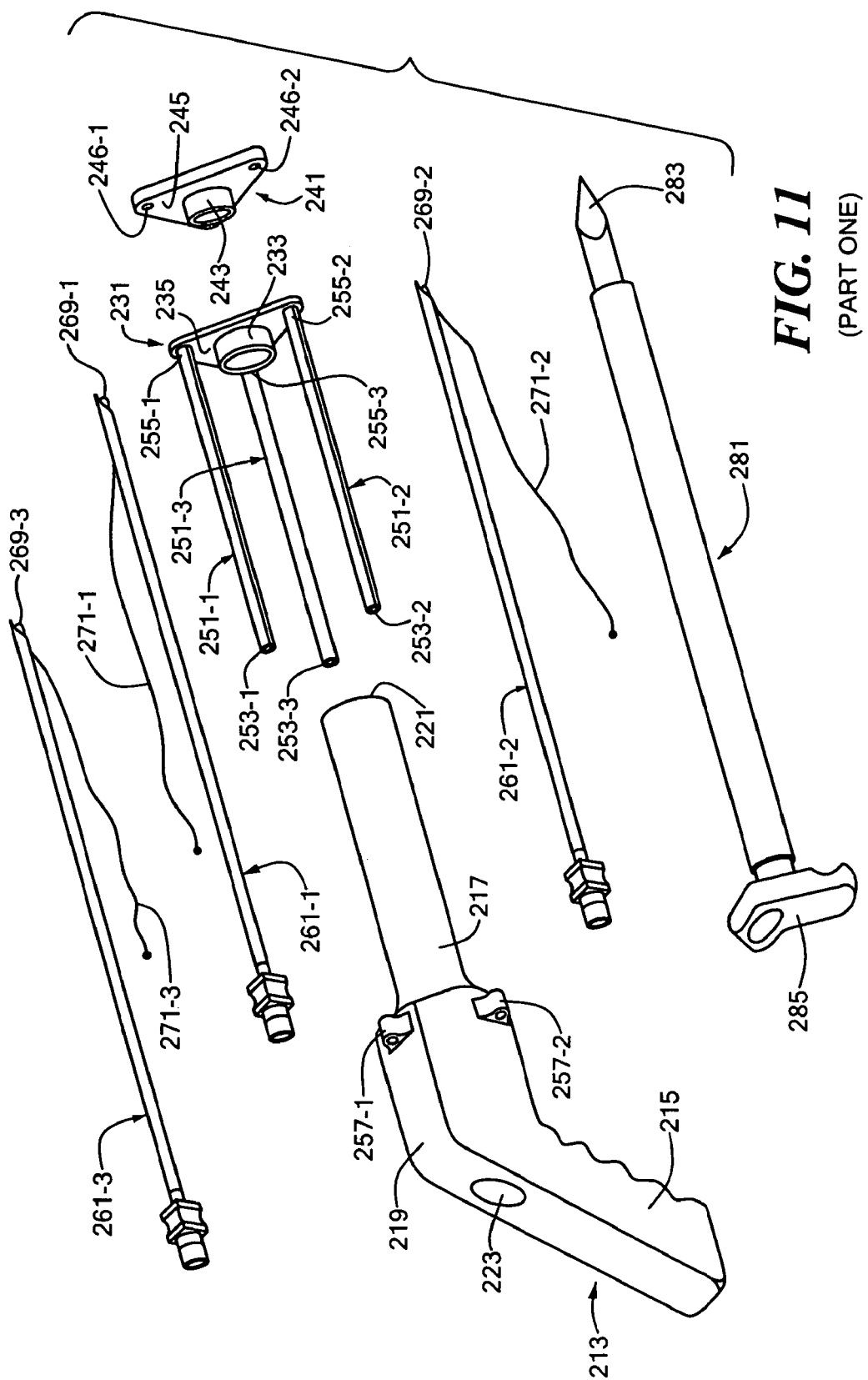
FIG. 11 (PART ONE)

(PART TWO)

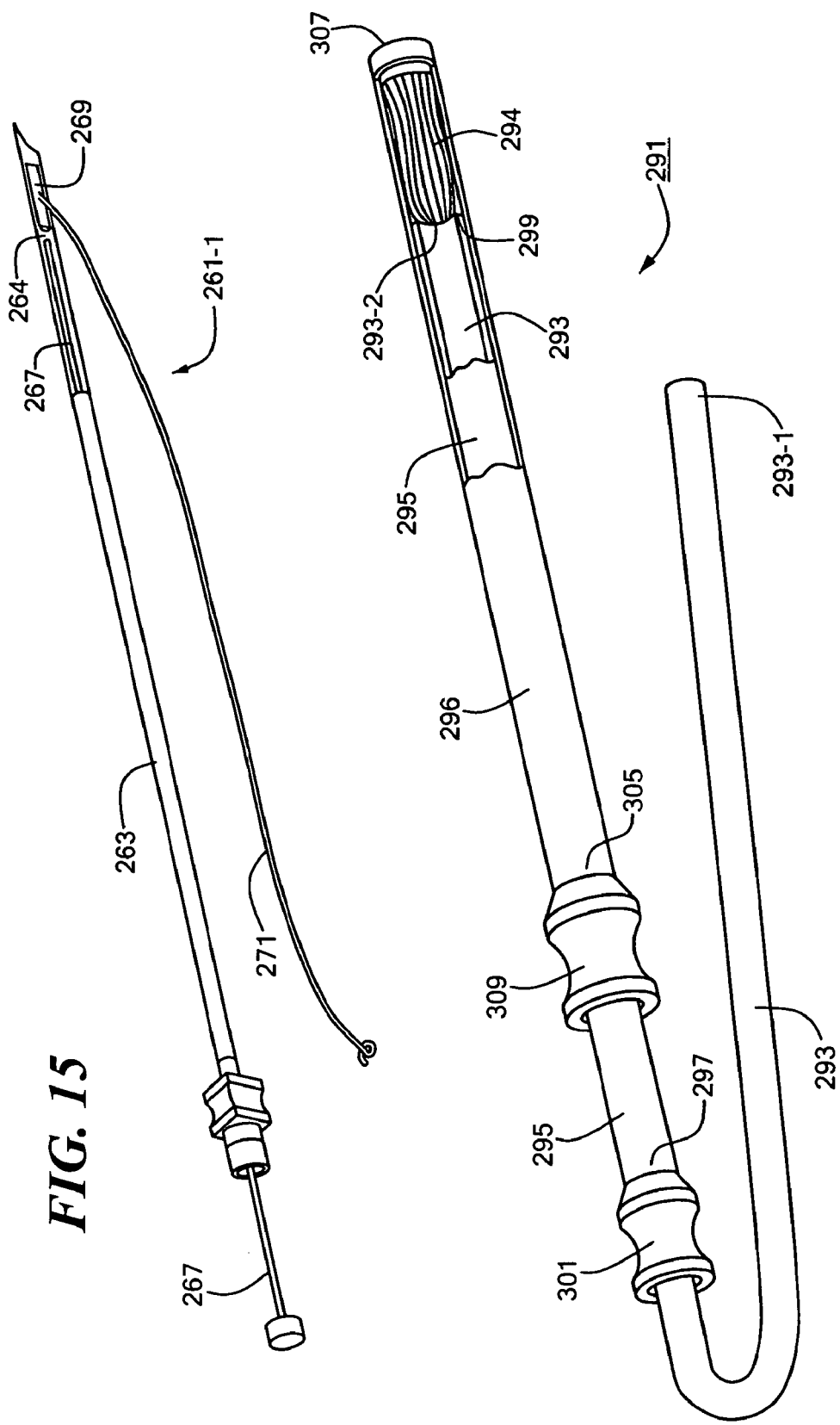

METHOD FOR PERCUTANEOUSLY IMPLANTING A MEDICAL CATHETER AND MEDICAL CATHETER IMPLANTING ASSEMBLY

CROSS-REFERENCE TO RELATED APPLICATIONS

This is a continuation of U.S. patent application Ser. No. 10/846,833 filed May 14, 2004, which is incorporated herein by reference in its entirety.

BACKGROUND OF THE INVENTION

The present invention relates generally to medical catheters and relates more particularly to a method for percutaneously implanting a medical catheter, such as a gastrostomy feeding tube, and to a medical catheter implanting assembly.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. Feeding is then typically performed by administering food through a catheter or feeding tube that has been inserted into the feeding tract, with the distal end of the feeding tube extending into the stomach and being retained therein by an internal anchor or bolster and the proximal end of the feeding tube extending through the abdominal wall.

Although gastrostomies were first performed surgically, most gastrostomies are now performed using percutaneous endoscopy and result in the implantation of a catheter/bolster assembly (also commonly referred to as a percutaneous endoscopic gastrostomy (PEG) device) in the patient. Two of the more common techniques for implanting a PEG device in a patient are "the push method" (also known as "the Sacks-Vine method") and "the pull method" (also known as "the Gauderer-Ponsky method"). Information regarding the foregoing two methods may be found in the following patents, all of which are incorporated herein by reference: U.S. Pat. No. 5,391,159, inventors Hirsch et al., which issued Feb. 21, 1995; U.S. Pat. No. 5,167,627, inventors Clegg et al., which issued Dec. 1, 1992; U.S. Pat. No. 5,112,310, inventor Grobe, which issued May 12, 1992; U.S. Pat. No. 4,900,306, inventors Quinn et al., which issued Feb. 13, 1990; and U.S. Pat. No. 4,861,334, inventor Nawaz, which issued Aug. 29, 1989.

According to the push method, the distal end of an endoscope is intubated (i.e., inserted) into a patient's mouth and is passed through the esophagus into the stomach. After distension of the stomach by inflation, an entry site on the abdomen is identified using the endoscope for transillumination, and an incision is made by passing the distal end of a needle coupled to an outer cannula (e.g., an angiocath needle or a Seldinger needle) through the abdominal and stomach walls and into the stomach. The proximal end of the outer cannula remains outside of the body and acts as a stop to prevent the proximal end of the needle from falling into the stomach. A snare is inserted into the stomach via the endoscope and is looped over the distal end of the needle. The snare is then "walked" up the needle until the outer cannula is snared. The snared cannula is then pulled proximally to tack the cannula to the stomach and, in turn, to secure the stomach wall to the abdominal wall. The needle is then removed while keeping the cannula in place. A first end of a flexible guidewire is then passed through the cannula and into the stomach where it is grasped by the snare, the second end of the guidewire remaining external to the patient. The endoscope and the snare are then withdrawn from the mouth of the patient to deliver the first end of the guidewire.

A push-type catheter implanting assembly is then inserted over the first end of the guidewire and is pushed over the guidewire towards its second end. The push-type catheter implanting assembly typically comprises a gastrostomy feeding tube, the gastrostomy feeding tube having a dome-shaped internal bolster disposed at its trailing end and having a tubular dilator serially connected to its leading end. The gastrostomy feeding tube and the internal bolster are typically made of a soft, biocompatible material, like silicone rubber, and may form a unitary structure. The dilator, which tapers in outer diameter from its trailing end to its leading end, is typically made of polyethylene or a like material which is stiffer than silicone but which still possesses some flexibility. Advancement of the push-type catheter implanting assembly over the guidewire continues until the front end of the dilator reaches the cannula and pushes the cannula out through the abdominal wall of the patient. The front end of the dilator is then pulled through the abdominal wall until the front end of the gastrostomy feeding tube emerges from the abdomen and, thereafter, the internal bolster at the rear end of the gastrostomy feeding tube engages the stomach wall. The guidewire is then removed from the patient. The clinician then re-intubates the patient with the endoscope and uses an optical channel in the endoscope to inspect whether the internal bolster is properly seated in the stomach.

If the internal bolster is properly placed against the stomach wall, a proximal portion of the implanted gastrostomy feeding tube is then typically cut and removed from the implanted tube to reduce the externally-extending portion of the tube to a desired length. (The removal of the proximal portion of the gastrostomy feeding tube also results in the removal of the dilator, which is connected thereto.) An external bolster is typically secured to the remaining implanted portion of the feeding tube to engage the abdomen in such a way as to prevent longitudinal movement of the feeding tube within the stoma tract. Additionally, a "Y-port" adapter is typically attached to the proximal end of the implanted feeding tube, the Y-port adapter being adapted to receive a pair of connector tips through which food and/or medications may be dispensed. In addition, a detachable locking clip is typically secured to the implanted feeding tube at a point between the external bolster and the Y-port adapter to prevent gastric fluids from escaping through the proximal end of the feeding tube when the feeding tube is not in use.

The pull method is similar in some respects to the above-described push method, the pull method differing from the push method in that, after the cannula is snared and the needle is removed therefrom, a first end of a suture is inserted through the cannula and into the stomach where it is grasped by the snare, the second end of the suture remaining external to the patient. The endoscope and the snare are then withdrawn from the mouth of the patient to deliver the first end of the suture. The first end of the suture is then coupled to the leading end of a pull-type catheter implanting assembly, the pull-type catheter implanting assembly typically comprising a gastrostomy feeding tube having an internal bolster at its trailing end and a plastic fitting at its leading end. The plastic fitting typically has a barbed rear portion mounted within the leading end of the feeding tube and a conical front portion that serves as a dilator, said conical front portion tapering in diameter from the leading end of the feeding tube to a front tip. A wire loop is fixed to the front tip of the plastic fitting, the first end of the suture being tied to the wire loop.

Using the second end of the suture, the pull-type catheter implanting assembly is then pulled retrograde through the patient until the gastrostomy feeding tube emerges from the abdomen of the patient and the internal bolster engages the stomach wall of the patient. Next, as is the case in the push method, the clinician then re-intubates the patient with the endoscope in order to visually inspect the placement of the internal bolster within the stomach. If the bolster is properly seated in the stomach, the implanted gastrostomy feeding tube is then typically cut to a desired length, an external bolster is typically secured to the cut implanted tube, a "Y-port" adapter is typically attached to the proximal end of the implanted feeding tube, and a detachable locking clip is typically secured to the implanted feeding tube at a point between the external bolster and the Y-port adapter.

Although the push and pull methods described above have achieved widespread use, particularly in the U.S., some people have expressed concern that the placement of a PEG device by the push method or the pull method may lead to infection of the stoma due to the fact that the PEG device is delivered to the stoma only after first being drawn through the patient's mouth, esophagus and stomach, all of which are unsterile environments populated by bacteria. Moreover, the push and pull methods described above require that an endoscope be introduced into the patient twice—first to deliver the snared guidewire or suture through the patient's mouth to the clinician and then again to permit a visual inspection of the placement of the internal bolster in the patient's stomach after the PEG device has been implanted. Unfortunately, the second intubation of the endoscope is often very difficult and/or painful because of damage caused during the first placement or due to the patient's anatomy or disease state.

In view of the above-described consequences associated with endoscopic placement of gastrostomy tubes, there has been some effort in devising a direct percutaneous approach to the placement of gastrostomy tubes.

Typically, such percutaneous approaches involve (i) inserting an endoscope into the patient and, through transillumination, identifying a desired insertion site; (ii) using sutures or T-fasteners, placed one at a time, to secure the abdominal wall to the stomach wall in a plurality of locations surrounding the future insertion site; (iii) using a scalpel to make an incision at the insertion site; (iv) using a series of dilators to enlarge the insertion site opening until said opening is large enough to pass therethrough the internal bolster at the distal end of a gastrostomy tube; and (v) sliding an external bolster over the proximal end of the gastrostomy tube down to skin level over the T-fastener wires or sutures.

Another type of percutaneous approach to the placement of a gastrostomy tube is disclosed in U.S. Pat. No. 6,030,264, inventors Durgin et al., which issued Feb. 29, 2000, and which is incorporated herein by reference. In this patent, there is disclosed a method and apparatus for the percutaneous placement of gastro-intestinal tubes, the apparatus comprising a longitudinal penetration device; a hollow, tapered dilator; and a sheath having a central lumen extending therethrough. The penetration device is placed within the sheath, pushed distally to penetrate the target organ, and then removed from the sheath. After the penetration device is removed, the dilator is inserted into the central lumen of the sheath until it penetrates the target organ, so that the sheath and the penetration device are radially dilated as the dilator passes through the sheath. The sheath is then pulled in the proximal direction to counterbalance the distal insertion force. A gastro-intestinal tube is inserted into the hollow center, and pushed distally until it exits the distal end of the dilator. The dilator and sheath are then removed from the target organ.

In addition, in U.S. Pat. No. 6,402,722, inventors Snow et al., which issued Jun. 11, 2002, and which is incorporated herein by reference, there is disclosed an apparatus and method for percutaneously placing gastrostomy tubes. The method enables percutaneous placement through an existing penetration, as well as placement where no penetration exists. The apparatus comprises a gastrostomy tube having an internal bolster which can be manipulated such that it has a reduced lateral extent; an axially-extending hollow sleeve which can surround the bolster to hold it in a position of reduced lateral extent; and a rip-cord capable of tearing the sheath. In a preferred embodiment, the internal bolster is folded to have a smaller diameter, the sleeve is placed over the bolster and shrunk down to a smaller diameter. The rip-cord runs distally along the outside of the tube, between the sleeve and the internal bolster, wraps over the distal end of the sleeve and runs proximally along the length of the tube. The replacement tube can then be pushed through a stoma. Once in place, the rip cord is pulled to tear away the sleeve, thereby allowing the bolster to revert to its original lateral extent.

Other documents of interest include U.S. Published Patent Application No. US-2004-0059293-A1, which was published Mar. 25, 2004, and which is incorporated herein by reference.

SUMMARY OF THE INVENTION

It is an object of the present invention to provide a novel medical catheter implanting assembly.

It is another object of the present invention to provide a medical catheter implanting assembly as described above that overcomes at least some of the problems described above in connection with existing medical catheter implanting assemblies, particularly medical catheter implanting assemblies of the type that are introduced into a patient's body endoscopically.

Therefore, according to one aspect of the invention, there is provided a medical catheter implanting assembly comprising (a) an outer sheath, said outer sheath having a proximal end and a distal end; (b) an inner sheath, said inner sheath having a proximal end and a distal end, said inner sheath being slidably mounted in said outer sheath; and (c) a medical catheter, said medical catheter having an internal bolster disposed at a distal end thereof, said medical catheter being inserted into said inner sheath, with said internal bolster being retained in a compressed state by said outer sheath; (d) whereby sliding movement of said outer sheath relative to said inner sheath releases said internal bolster from said compressed state.

According to another aspect of the invention, there is provided a medical catheter implanting assembly comprising (a) a dilator, said dilator having a proximal end and a distal end, said proximal end being shaped to define a cavity; (b) a stiffening sheath, said stiffening sheath having a proximal end and a distal end; and (c) a medical catheter, said medical catheter having an internal bolster disposed at a distal end thereof, said medical catheter being inserted into said stiffening sheath, with said internal bolster being retained in a compressed state in said cavity.

The present invention is also directed to a novel method for percutaneously implanting a medical catheter.

For purposes of the present specification and claims, various relational terms like "top," "bottom," "proximal," "distal," "upper," "lower," "front," and "rear" are used to describe the present invention when said invention is positioned in or viewed from a given orientation. It is to be understood that, by altering the orientation of the invention, certain relational terms may need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIG. 6 is a side view of a second embodiment of a medical catheter implanting assembly constructed according to the teachings of the present invention;

FIG. 7 is a longitudinal section view of the medical catheter implanting assembly shown in FIG. 6;

FIG. 10 is a perspective view of a third embodiment of a medical catheter implanting assembly constructed according to the teachings of the present invention, the fasteners of the needle assemblies not being shown;

FIG. 15 is a perspective view, broken away in part, of the needle assembly shown in FIG. 10, the plunger of the needle assembly being shown in a retracted position; and FIG. 16 is a perspective view, broken away in part, of the feeding tube assembly shown in FIG. 10, said feeding tube assembly being shown with the internal bolster in a compressed state.

DETAILED DESCRIPTION OF PREFERRED EMBODIMENTS

Figure 1:
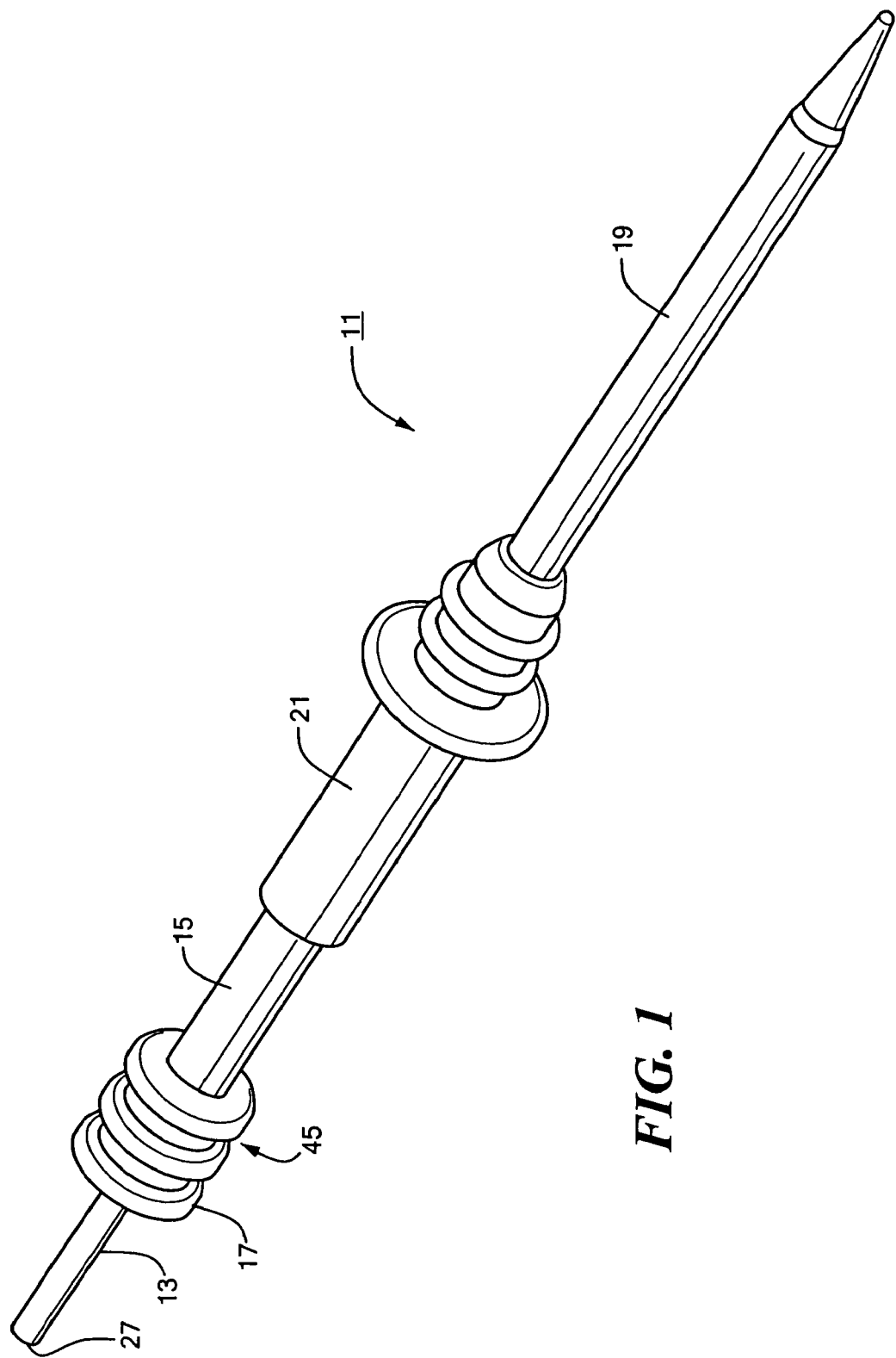
FIG. 1 is a perspective view of a first embodiment of a medical catheter implanting assembly constructed according to the teachings of the present invention, the medical catheter implanting assembly being shown in its retracted position.
Figure 2:
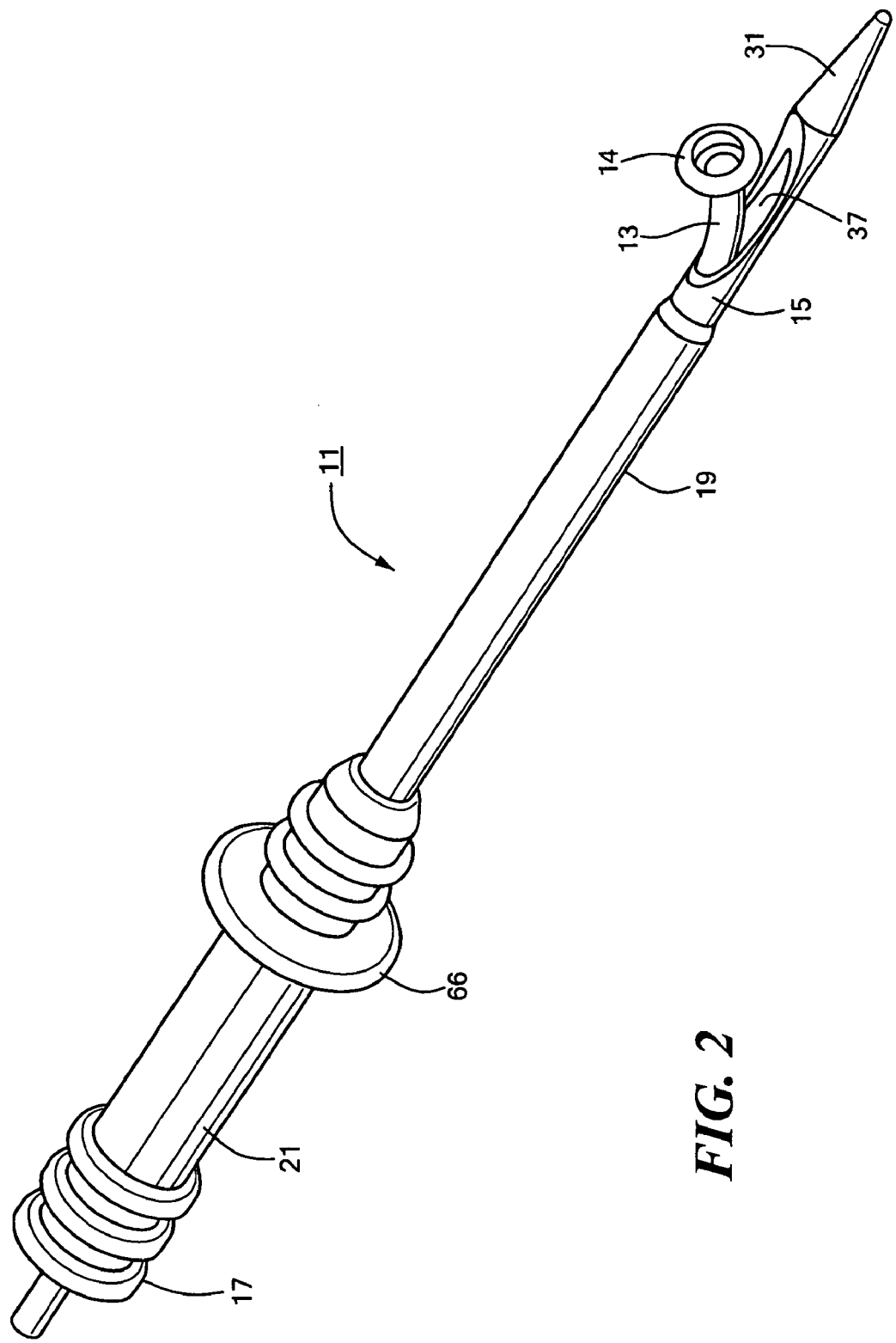
FIG. 2 is a perspective view of the medical catheter implanting assembly shown in FIG. 1, the medical catheter implanting, assembly being shown in its advanced or deployed position.
Figure 3:
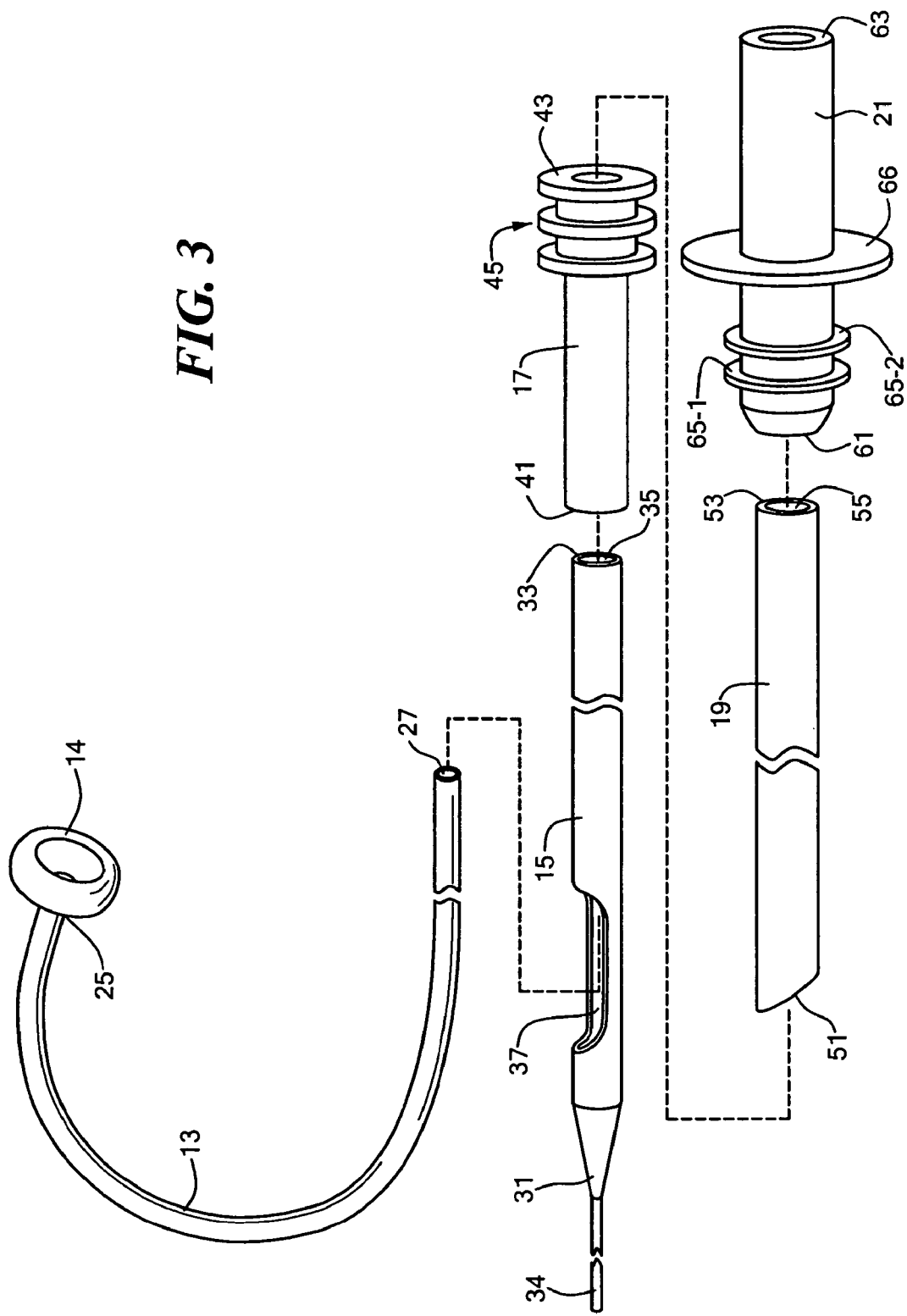
FIG. 3 is a fragmentary, partially exploded, perspective view of the medical catheter implanting assembly shown in FIG. 1.
Figure 4:
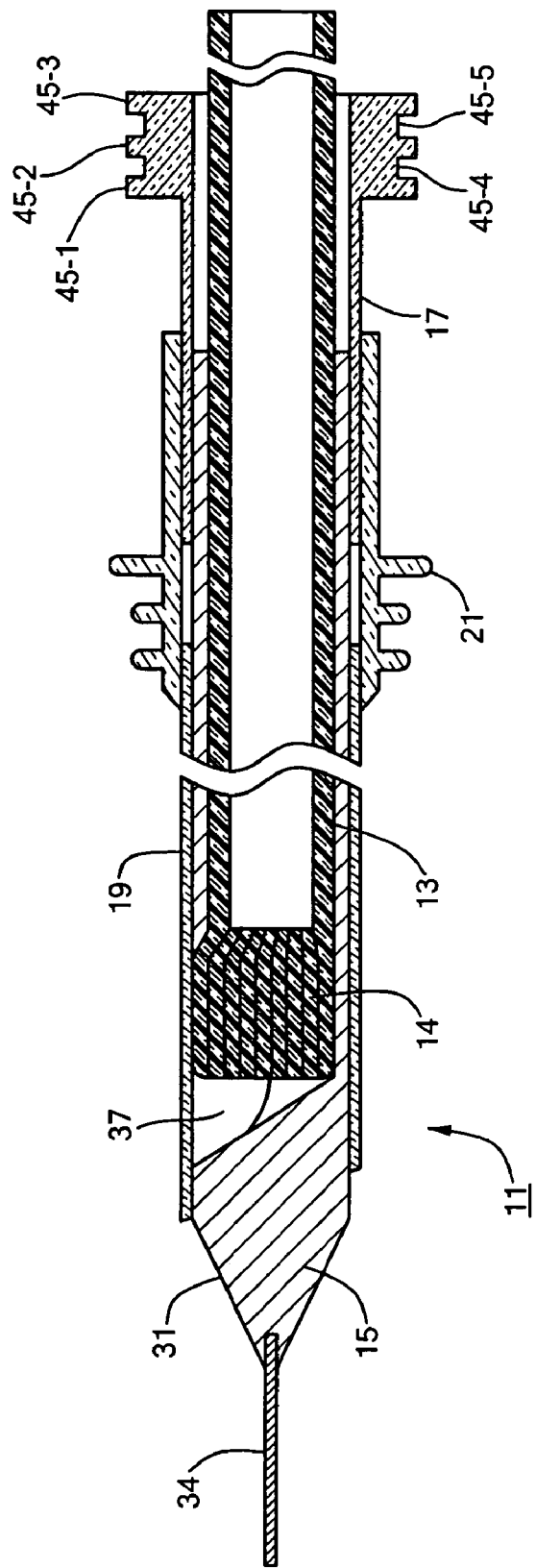
FIG. 4 is a fragmentary, longitudinal section view of the medical catheter implanting assembly shown in FIG. 1, the medical catheter implanting assembly being shown in its retracted position.

Referring now to FIGS. 1 through 4, there are shown various view of a first embodiment of a medical catheter implanting assembly constructed according to the teachings of the present invention, said medical catheter implanting assembly being represented generally by reference numeral 11.

Assembly 11 includes a gastrostomy feeding tube 13, an internal bolster 14, an inner sheath 15, an inner sheath handle 17, an outer sheath 19 and an outer sheath handle 21.

Tube 13, which may be a conventional gastrostomy feeding tube, is an elongated, tubular member preferably made of a soft, biocompatible, silicone rubber. Tube 13 has a distal end 25 and a proximal end 27. A series of ruler markings (not shown) are printed on tube 13 and extend several inches from distal end 25 in the direction of proximal end 27 to facilitate the cutting of tube 13 to a desired length (after tube 13 has been implanted in a patient).

Internal bolster 14, which is also made of a soft, biocompatible, silicone rubber, is an enlarged, dome-shaped member securely disposed at distal end 25 of tube 13 for use in anchoring distal end 25 of tube 13 within a patient. In the present embodiment, bolster 14 forms a unitary structure with tube 13. As can readily be appreciated, bolster 14 may be modified to come in a variety of different shapes and sizes and, if desired, may be replaced with a balloon-type bolster or other bolster that is transformable between an expanded anchoring state and a collapsed state.

Inner sheath 15, which is an elongated, unitary member, preferably made of a substantially rigid, biocompatible plastic (e.g., a high durometer polyethylene or polypropylene), includes a conical distal end 31 and a straight proximal end 33. A short length of wire 34, the purpose of which will be discussed below, is insert-molded into distal end 31 and extends distally therefrom. A bore 35 extends longitudinally from proximal end 33 in the direction of distal end 31, bore 35 terminating a short distance before distal end 31. For reasons to become apparent below, bore 35 is appropriately dimensioned to slidably receive gastrostomy feeding tube 13. A transverse window 37 having a scalloped shape is provided in inner sheath 15, window 37 communicating with bore 35 at its distal end.

Inner sheath handle 17, which is an elongated, tubular, unitary member, preferably made of a rigid plastic, includes a distal end 41 and a proximal end 43. Distal end 41 of handle 17 is inserted over proximal end 33 of inner sheath 15 and is securely fixed thereto. Proximal end 43 of handle 17 is shaped to include an annular embossment 45 which facilitates the gripping of handle 17 by a user and, as will become apparent below, acts as a stop to limit distal movement of inner sheath 15, embossment 45 being shaped to include three larger diameter rings 45-1 through 45-3 separated by two smaller diameter rings 45-4 and 45-5.

Outer sheath 19, which is an elongated, tubular, unitary member, preferably made of a substantially rigid, lubricious, biocompatible material (e.g., polytetrafluoroethylene), includes a beveled distal end 51 and a straight proximal end 53. A longitudinal bore 55 extends from distal end 51 to proximal end 53, bore 55 being appropriately dimensioned to slidably receive inner sheath 17.

Outer sheath handle 21, which is an elongated, tubular, unitary member, preferably made of a rigid plastic, includes a distal end 61 and a proximal end 63. Distal end 61 of handle 21 is inserted over proximal end 53 of outer sheath 19 and is securely fixed thereto. A plurality of annular embossments 65-1, 65-2 and 66 are formed on the outer surface of handle 21 to facilitate the gripping of handle 21 by a user.

To assemble assembly 11, handle 17 is secured to inner sheath 15, and handle 21 is secured to outer sheath 19. Then, wire 34 and distal end 31 of inner sheath 15 are inserted in a distal direction through handle 21 and outer sheath 19. Next, proximal end 27 of tube 13 is inserted through window 37 and into bore 35 of inner sheath 15. The remainder of tube 13 is then fed through window 37 and into bore 35 until proximal end 27 of tube 13 emerges from handle 17 and bolster 14 is positioned just outside of window 37. Bolster 14 is then compressed and tucked tightly into window 37 as tube 13 is tensioned proximally and distal end 51 of outer sheath 19 is moved distally over window 37, sheath 19 serving to retain bolster 14 in window 37.

Referring now to FIGS. 5(a) through 5(h), the manner in which assembly 11 may be used to percutaneously implant tube 13 in a patient is illustrated. First, an endoscope E is inserted into the stomach of the patient and is used to transilluminate an incision site. An incision is then made by passing the distal end of a needle N coupled to a peelable cannula C through the abdominal wall A and the stomach wall S and into the stomach (see FIG. 5(a)). Then, a snare L is inserted into the stomach via endoscope E and is looped over the distal end of needle N (see FIG. 5(b)). Snare L is then "walked" up needle N until peelable cannula C is snared. The snared cannula C is then pulled to tack cannula C to abdominal wall A and, in turn, to tack abdominal wall A to stomach wall S. Needle N is then removed while keeping peelable cannula C in place (see FIG. 5(c)). One to four T-fasteners F are then used to provide further securing of abdominal wall A to stomach wall S (see FIG. 5(d)).

Figure 5A:
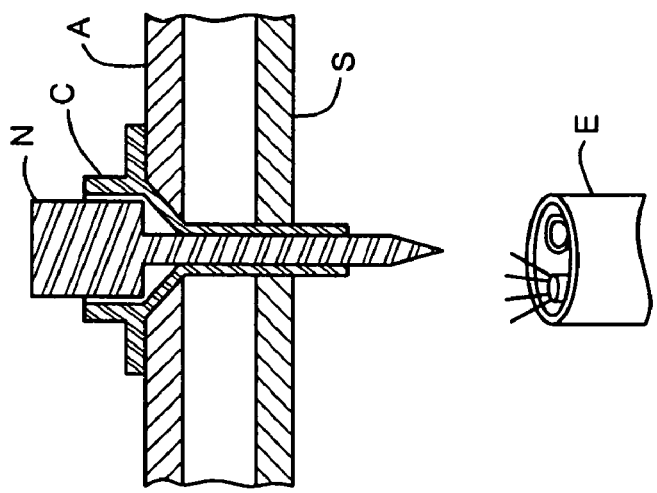
FIGS. 5(a) through 5(h) are schematic side views, partly in section, illustrating the operation of the medical catheter implanting assembly of FIG. 1.
Figure 5B:
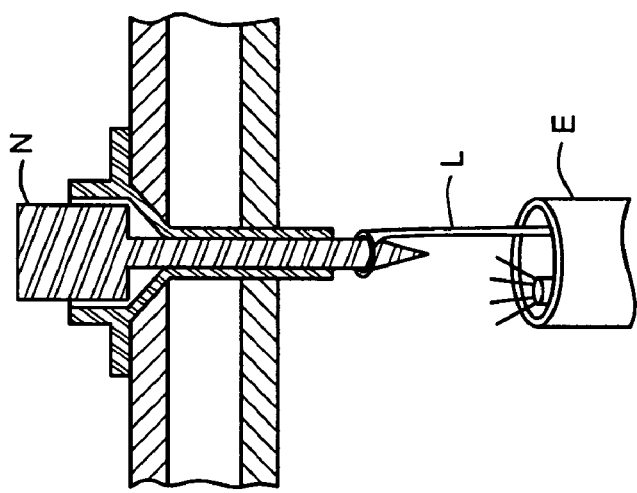
Figure 5C:
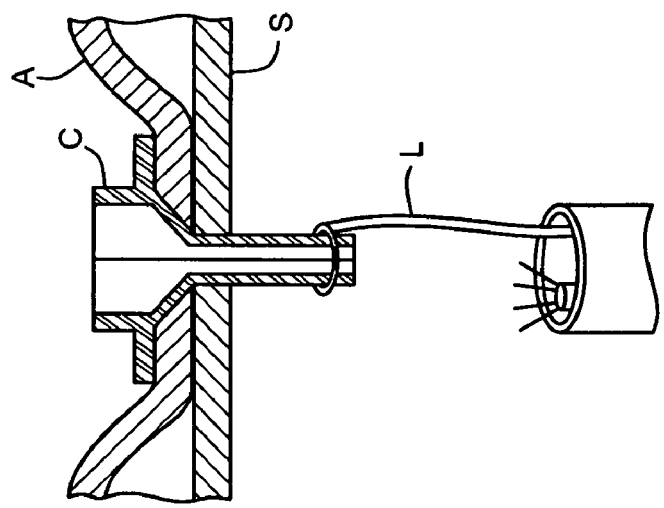
Figure 5F:
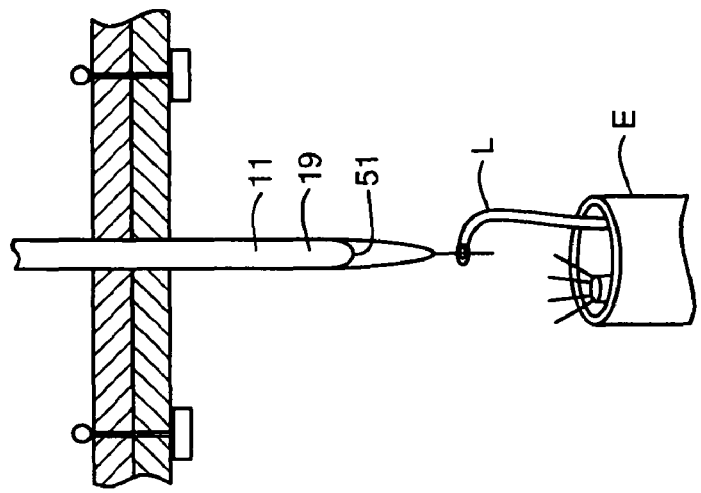
Figure 5E:
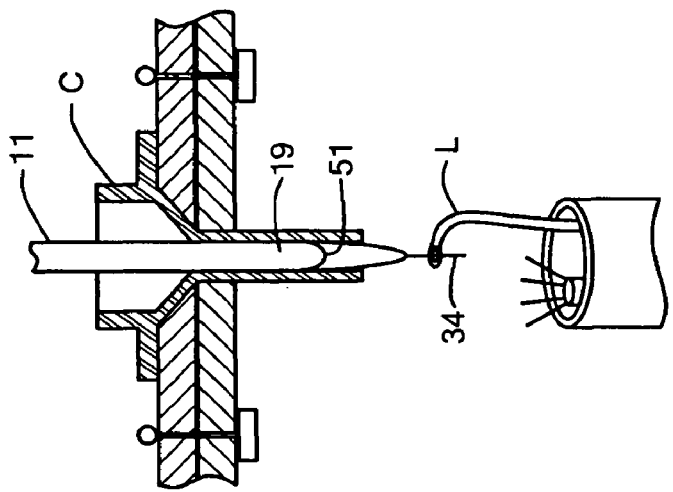
Figure 5D:
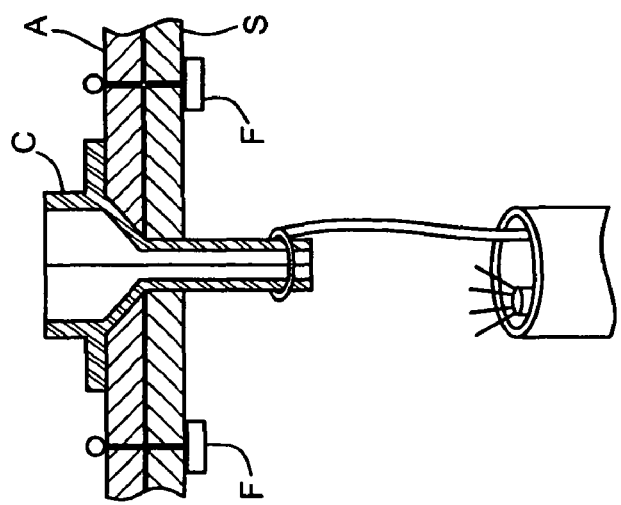
Figure 5H:
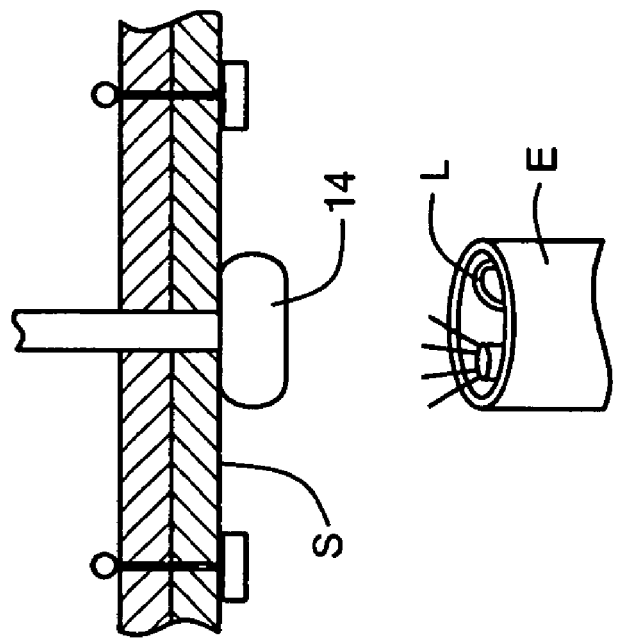
Figure 5G:
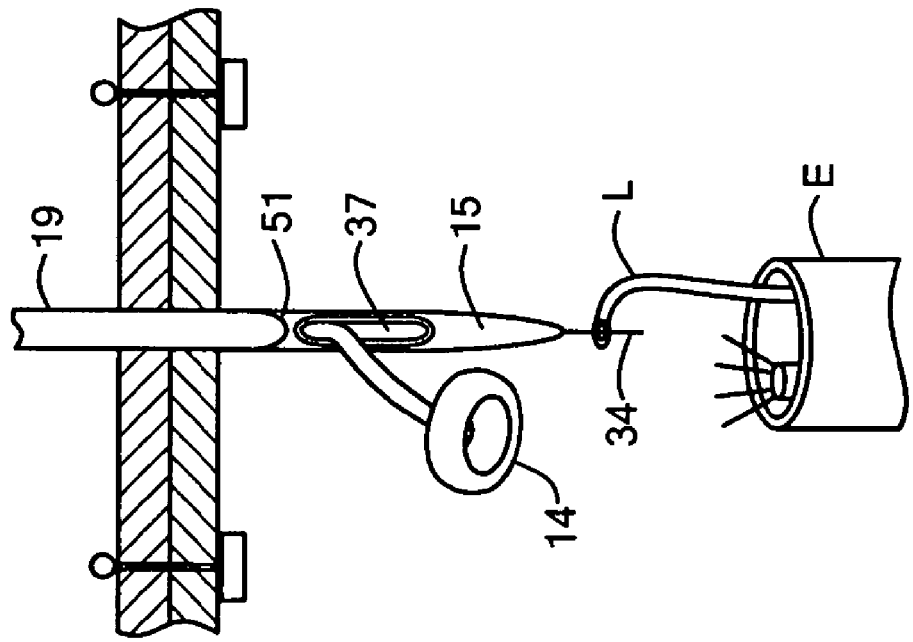

Next, the distal end of assembly 11 is inserted through peelable cannula C and into the stomach, and snare L is moved from peelable cannula C to wire 34 (see FIG. 5(e)). Peelable cannula C is then peeled in half and removed laterally in two pieces from the incision site, and assembly 11 is inserted further into the stomach (both by pushing assembly 11 from outside the patient and by using snare L to pull assembly 11 from inside the patient) until distal end 51 of outer sheath 19 can be seen by endoscope E (see FIG. 5(f). Then, using handle 21 to keep outer sheath 19 stationary, handle 17 is used to move inner sheath 15 distally relative to outer sheath 19 until window 37 is advanced beyond distal end 51 of outer sheath 19. With window 37 no longer covered by outer sheath 19, bolster 14 immediately springs back to its decompressed shape, which is larger than window 37; as a result, bolster 14 exits window 37 (see FIG. 5(g)). Snare L is then removed from wire 34 and retracted into endoscope E, and inner sheath 15 and outer sheath 19 are removed from the patient, allowing bolster 14 to engage the stomach wall S (see FIG. 5(h)). Endoscope E is then used to image the placement of bolster 14. Assuming that bolster 14 is placed properly, endoscope E is then removed from the patient.

As can be seen, one benefit to using assembly 11 is that the gastrostomy feeding tube is not fed through the mouth, esophagus and stomach of the patient and, therefore, does not suffer from the possible complications resulting from microbial contamination of the feeding tube. Another benefit is that the endoscope does not need to be intubated into the patient twice, but rather, may be inserted into the patient and then remain in the patient throughout the implantation and inspection processes.

Although assembly 11 has been described herein in the context of gastrostomy feeding, assembly 11 is not limited to gastrostomy feeding and may be used for other types of feeding, as well as for drainage.

Also, it should be understood that, although bolster 14 has been described herein as a self-expandable, mushroom-shaped or dome-shaped bolster, bolster 14 could be replaced with a conventional balloon-type bolster or a bolster having a malecot structure.

Figure 8:
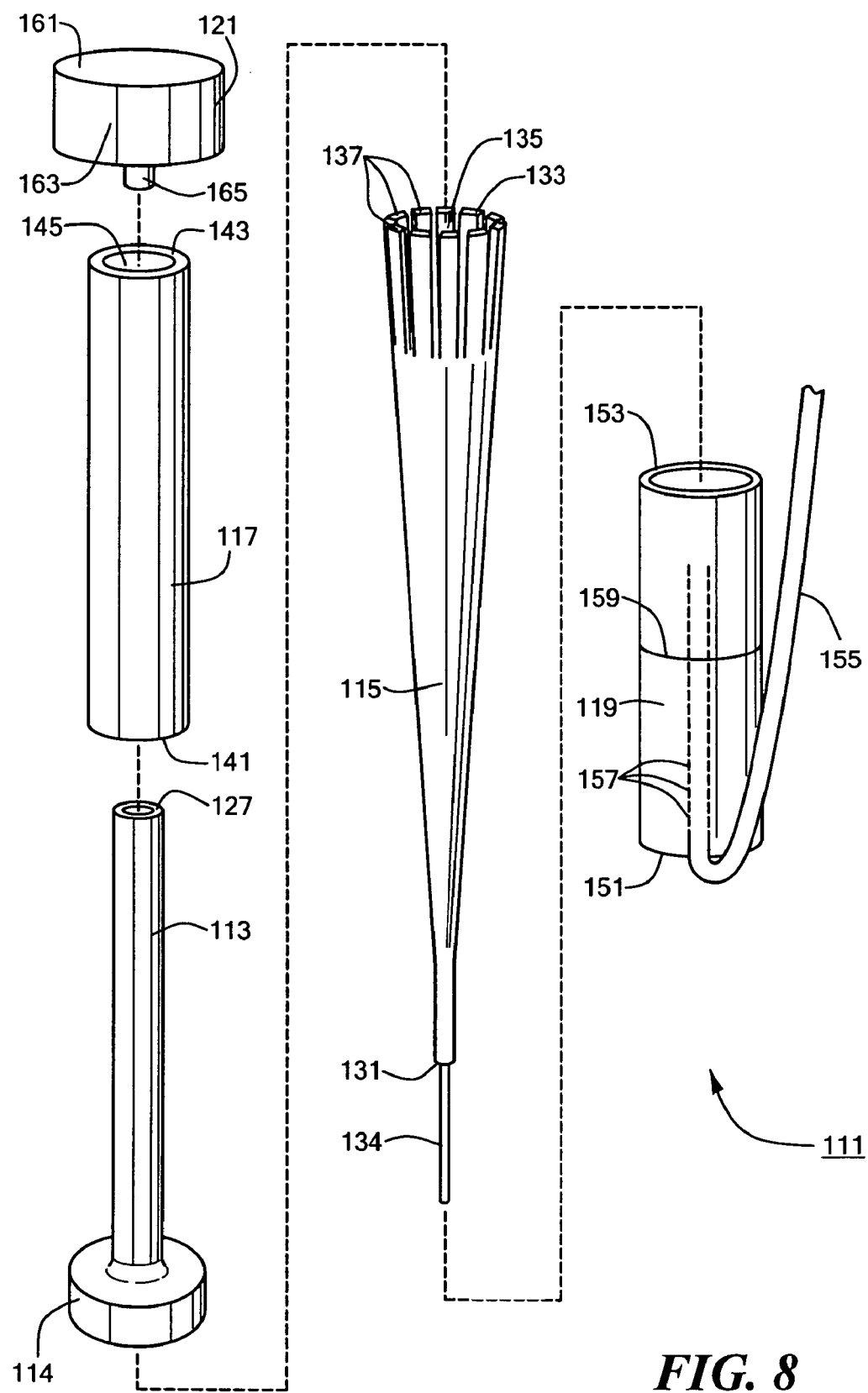
FIG. 8 is a partially exploded perspective view of the medical catheter implanting assembly shown in FIG. 6.

Referring now to FIGS. 6 through 8, there are shown various views of a second embodiment of a medical catheter implanting assembly constructed according to the teachings of the present invention, said medical catheter implanting assembly being represented generally by reference numeral 111.

Assembly 111 includes a gastrostomy feeding tube 113, an internal bolster 114, a dilator 115, a stiffening sheath 117, a length of shrink tubing 119 and a cap 121.

Gastrostomy feeding tube 113 and internal bolster 114 may be identical to gastrostomy feeding tube 13 and bolster 14, respectively, of assembly 11.

Dilator 115, which is an elongated, generally conical, unitary member, preferably made of a substantially rigid, biocompatible plastic (e.g., a high durometer polyethylene or polypropylene), includes a distal end 131 and a proximal end 133. A short length of wire 134, the purpose of which will be discussed below, is insert-molded into distal end 131 and extends distally therefrom. A small cavity 135 is centrally provided in proximal end 133 and extends a short distance distally, cavity 135 being surrounded by a plurality of flexible fingers 137. As will be described further below, bolster 114, in its compressed state, is received within cavity 135.

Stiffening sheath 117, which is an elongated, tubular, unitary member, preferably made of a rigid, biocompatible plastic, has a distal end 141, a proximal end 143 and a longitudinal bore 145. Sheath 117, which is inserted over tube 113 to provide column strength to tube 113, has a length such that bolster 114 extends just beyond distal end 141 of sheath 117 and such that a proximal end 127 of tube 113 extends just beyond proximal end 143 of sheath 117. As will be discussed further below, the diameter of bore 145 is slightly greater than the relaxed outer diameter of tube 113. Sheath 117 has an outer diameter approximating that of dilator 115 at its proximal end 133, and distal end 141 of sheath 117 is positioned on top of fingers 137 of dilator 115.

Shrink tubing 119, which is an elongated, tubular, unitary member, preferably made of a biocompatible, heat-shrinkable material, includes a distal end 151 and a proximal end 153. Distal end 151 of shrink tubing 119 is inserted over and radially compresses fingers 137, thereby retaining bolster 114 in its compressed state within cavity 135. Proximal end 153 of shrink tubing 119 is inserted over stiffening sheath 117 at an intermediate point along its length. A distally extending tab or pull cord 155 is integrally formed on shrink tubing 119 at distal end 151, cord 155 being provided to enable one to tear shrink tubing 119 for reasons to be described below. Perforations 157 extending proximally from pull cord 155 are additionally provided on shrink tubing 119 to facilitate the tearing of shrink tubing 119 using pull chord 155. Preferably, such perforations 157 do not continue proximally all the way to proximal end 153 since it is desirable for shrink tubing 119 to remain tightly fixed to sheath 117 in order that tubing 119 may be removed from the patient with sheath 117. A marking 159 is preferably circumferentially provided on the outer surface of tubing 119, marking 159 denoting the location of internal bolster 114 within dilator 115.

Cap 121, which is a unitary member, preferably made of a rigid, biocompatible plastic, is shaped to include a circular top wall 161, a circular side wall 163 and a centrally disposed circular plug 165. Plug 165 is appropriately dimensioned so that the insertion of plug 165 into proximal end 127 of tube 113 forces proximal end 127 of tube 113 radially outwardly against stiffening sheath 117, thereby securing proximal end 127 of tube 113 to sheath 117. Such a coupling of proximal end 127 of tube 113 to sheath 117 provides a desirable safety feature as it deters proximal end 127 of tube 113 from being drawn accidentally into the stomach of a patient if assembly 111 somehow malfunctions during the launching of tube 113 and dilator 115 does not separate from bolster 114. As can readily be appreciated, cap 121 also serves to prevent matter from entering tube 113 prior to the implanting of tube 113 in a patient.

To assemble assembly 111, tube 113 is inserted into sheath 117 so that bolster 114 extends distally beyond sheath 117 and so that proximal end 127 of tube remains proximal to sheath 117. The proximal end 127 of tube 113 is then secured to sheath 117 using cap 121. Bolster 114 is then compressed and inserted into cavity 135 of dilator 115. Then, while fingers 137 are radially compressed against bolster 114, shrink tubing 119 is inserted over and applied to distal end 141 of sheath 117 and proximal end 143 of dilator 115.

Referring now to FIGS. 9(a) through 9(i), the manner in which assembly 111 may be used to percutaneously implant tube 113 in a patient is illustrated. First, an endoscope E is inserted into the stomach of the patient and is used to transilluminate an incision site. An incision is then made by passing the distal end of a needle N coupled to a peelable cannula C through the abdominal wall A and the stomach wall S and into the stomach (see FIG. 9(a)). Then, a snare L is inserted into the stomach via endoscope E and is looped over the distal end of needle N (see FIG. 9(b)). Snare L is then "walked" up needle N until peelable cannula C is snared. The snared cannula C is then pulled to tack cannula C to abdominal wall A and, in turn, to tack abdominal wall A to stomach wall S. Needle N is then removed while keeping peelable cannula C in place (see FIG. 9(c)). One to four T-fasteners F are then used to provide further securing of abdominal wall A to stomach wall S (see FIG. 9(d)).

Figure 9C:
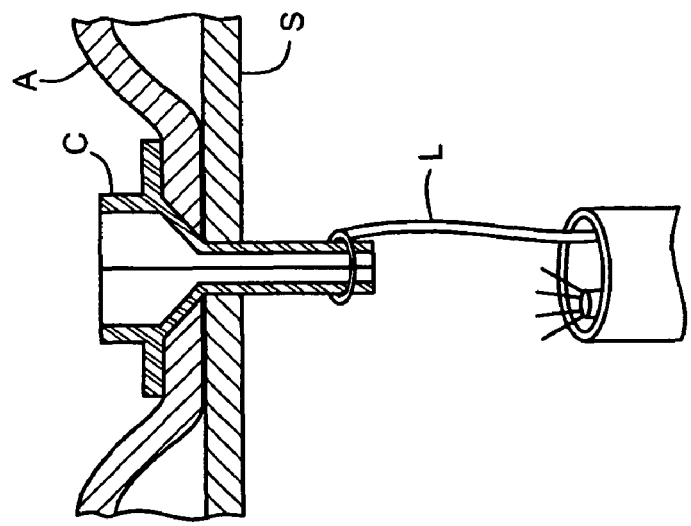
FIGS. 9(a) through 9(i) are side views, partly in section, illustrating the operation of the medical catheter implanting assembly of FIG. 6.
Figure 9B:
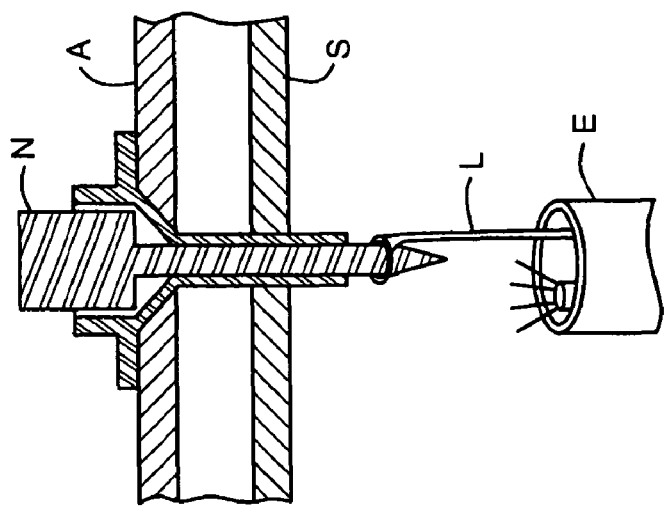
Figure 9A:
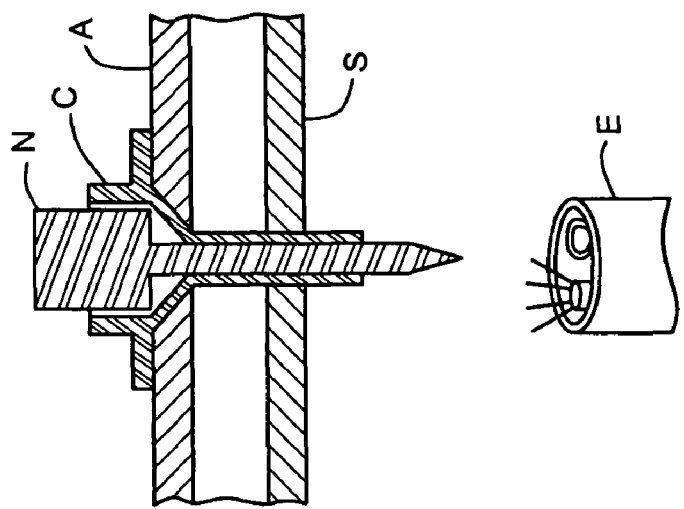
Figure 9F:
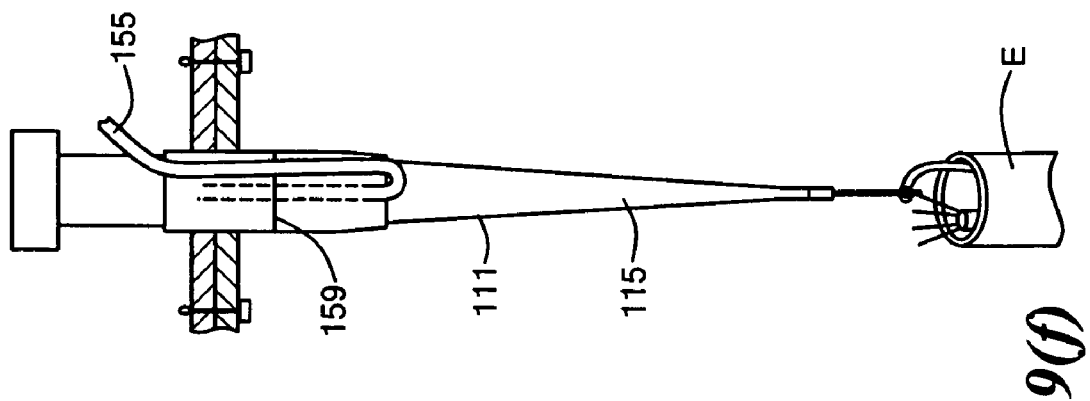
Figure 9E:
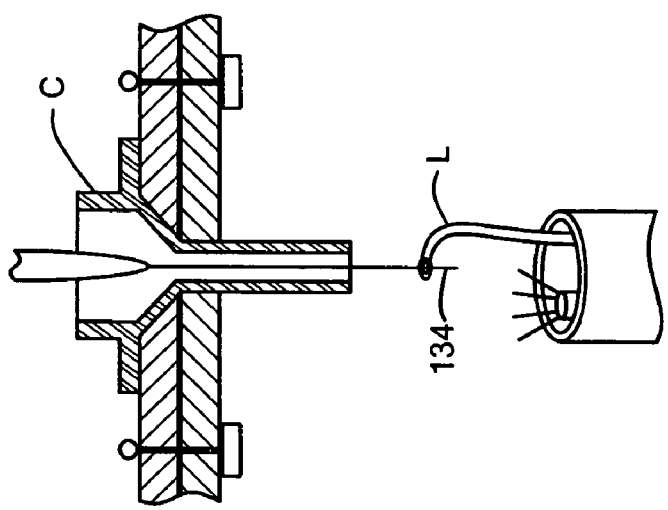
Figure 9D:
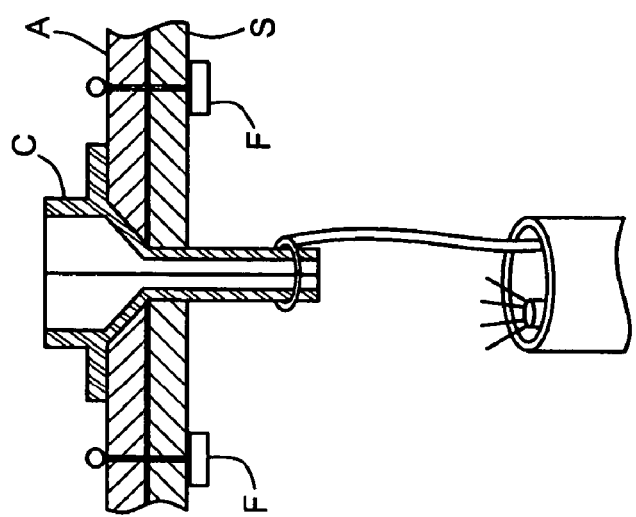
Figure 9I:
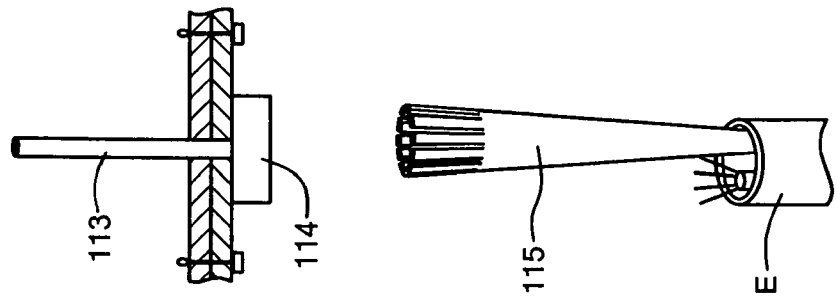
Figure 9H:
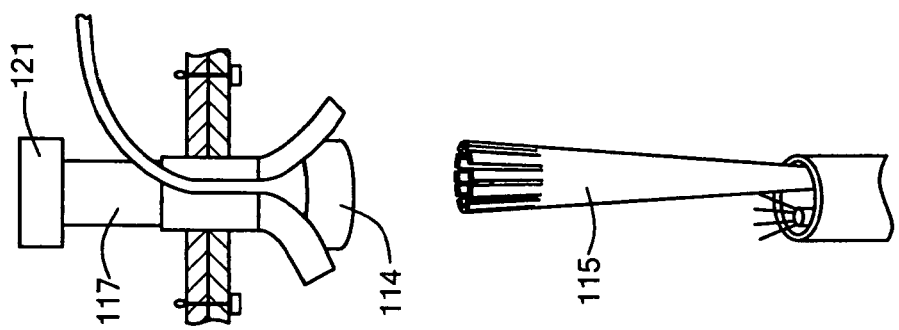
Figure 9G:
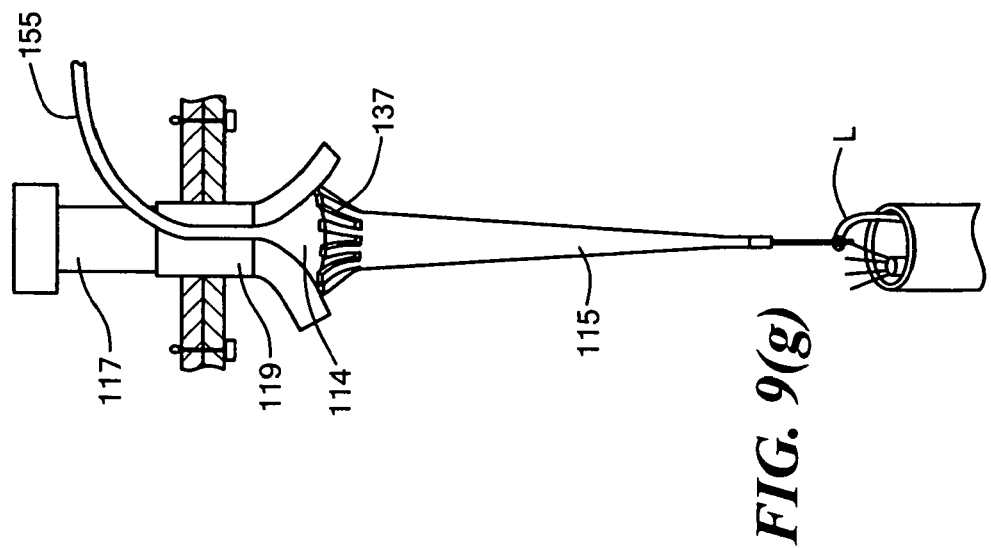

Next, wire 134 is inserted through peelable cannula C and into the stomach, and snare L is moved from peelable cannula C to wire 134 (see FIG. 9(e)). Peelable cannula C is then peeled in half and removed laterally in two pieces from the incision site, and assembly 111 is inserted further into the stomach (both by pushing assembly 111 from outside the patient and by using snare L to pull assembly 111 from inside the patient) until marking 159 can be seen by endoscope E (see FIG. 9(f)). Then, while snare L is used to keep dilator 115 stationary, pull cord 155, the free end of which is positioned outside of the patient, is pulled proximally to rip the distal portion of shrink tubing 119 (the proximal portion of shrink tubing 119 preferably remaining secured to sheath 117). With shrink tubing 119 thus ripped and no longer radially compressing flexible fingers 137, fingers 137 cannot keep bolster 114 in its compressed state. Consequently, bolster 114 decompresses and begins to emerge from cavity 135 of dilator 115 (see FIG. 9(g)). Next, while keeping tube 113 stationary, for example, by placing one's thumb on cap 121 and the remaining fingers of one's hand on sheath 117, snare L is used to completely remove dilator 115 from bolster 114, thereby allowing bolster 114 to engage the stomach wall S (see FIG. 9(h)). Next, cap 121 is removed from proximal end 127 of tube 113 to decouple tube 113 from sheath 117, and sheath 117 and tubing 119 are then slid proximally off tube 113. Endoscope E is then used to image the placement of bolster 114 (see FIG. 9(i)). Assuming that bolster 114 is placed properly, endoscope E and the snared dilator 115 are then removed from the patient.

It should be understood that, although dilator 115 of the present embodiment is shown having a certain length, dilator 115 could be modified to have a comparatively smaller length. In fact, one alternative dilator is a solid, short member that does not include a finger-surrounded cavity into which the bolster fits. Instead, the dilator proximally terminates at a flat, solid end with a protruding rod, the bolster being compressed centrally around this protruding rod. The shrink tubing keeps the bolster compressed around this protruding rod since it covers the distal end of the stiffening sheath, the compressed bolster and the proximal end of the dilator. The bolster is then released by pulling the pull cord in the shrink tubing as described above.

Another alternative dilator differs from dilator 115 in that fingers 137 are replaced with a solid wall. The cavity in which the bolster is received may be treated with a lubricious coating which allows the bolster to exit the cavity with little friction upon launch.

In addition, it should be understood that dilator 115 could be made of a biodegradable material and/or that wire 134 could be replaced with a loop of the type used in a pull-type catheter implanting assembly. Where dilator 115 is made of a biodegradable material, the launching of the tube and its internal bolster could be actuated by biodegradation of dilator 115.

Also, it should be noted that, instead of having an integrally formed pull cord, one could have a pull cord comprising a string conventionally positioned for such a purpose.

Moreover, instead of retaining bolster 114 in the manner shown in assembly 111, one could enclose bolster 114 in a chamber/tube that, upon the generation of pressure, splits at the seams, thereby exposing the bolster.

Furthermore, instead of using a feeding tube having a self-expandable, mushroom-shaped or dome-shaped bolster like bolster 114, one could use a feeding tube having an inflatable balloon-type bolster. The use of such a bolster would obviate the need to positively compress the bolster to a smaller size during delivery of the bolster through the stoma. Alternatively, one could use an internal bolster having a malecot structure.

Lastly, although assembly 111 has been described herein in the context of gastrostomy feeding, assembly 111 is not limited to gastrostomy feeding and may be used for other types of feeding, as well as for drainage.

As discussed above in connection with the use of assemblies 11 and 111, it is highly desirable to fasten the abdominal wall to the stomach wall prior to the insertion of assembly 11 or assembly 111 into the patient. Such fastening deters movement of the stomach wall away from the abdominal wall during insertion of the distal end of the assembly into the patient, said movement being undesirable as it may possibly result in the insertion holes in the abdominal and stomach walls coming out of alignment with one another and the assembly not being inserted into the stomach. If this occurs, either one must attempt the difficult task of locating the existing insertion hole in the stomach wall and inserting the assembly therethrough or one must create a second insertion hole in the stomach wall.

In addition, as explained above in connection with existing percutaneous gastrostomy placement techniques that involve the use of a scalpel to make an incision and then a series of increasingly large dilators to make an opening through which an internal bolster may be inserted, such fasteners are also typically used to fasten the abdominal and stomach walls to one another prior to the use of a scalpel to make the incision. Examples of such fasteners are disclosed in U.S. Pat. Nos. 5,341,823 and 4,705,040, both of which are incorporated herein by reference. Typically, such fasteners are independently placed at locations surrounding the future incision site.

Figure 11:
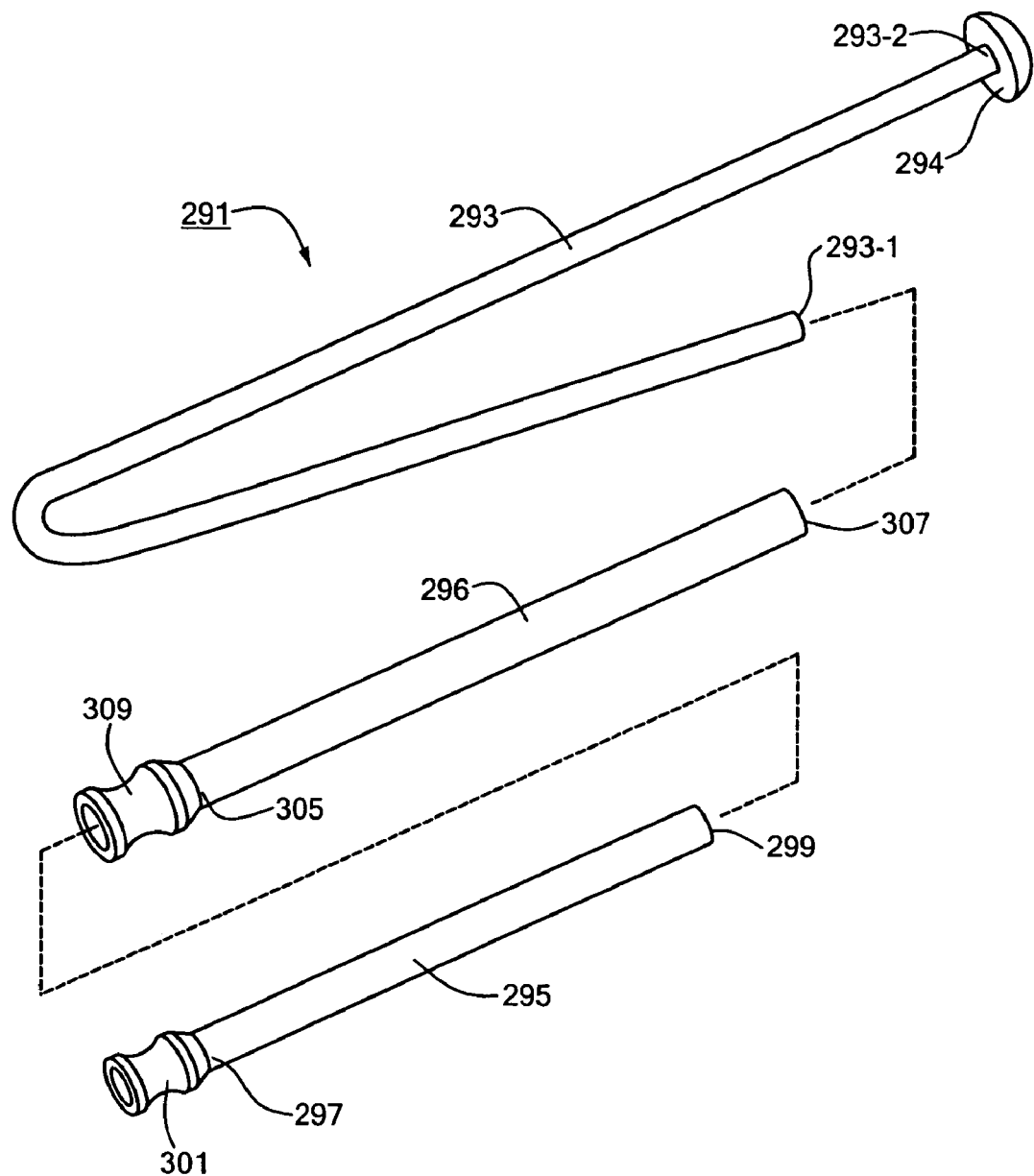
FIG. 11 is a partially exploded, perspective view of the medical catheter implanting assembly shown in FIG. 10.

Referring now to FIGS. 10 and 11, there are shown perspective and partially exploded perspective views of a third embodiment of a medical catheter implanting assembly constructed according to the teachings of the present invention, said medical catheter implanting assembly being represented generally by reference numeral 211.

Assembly 211 includes a gun-shaped casing 213, casing 213 preferably being made of a rigid metal or plastic and comprising a handle portion 215 and a barrel portion 217. Barrel portion 217, which is shaped to include a proximal portion 219 of comparatively greater outer diameter and a distal portion 221 of comparatively smaller outer diameter, includes a longitudinal bore 223 extending entirely through proximal portion 219 and distal portion 221.

Figure 12A:
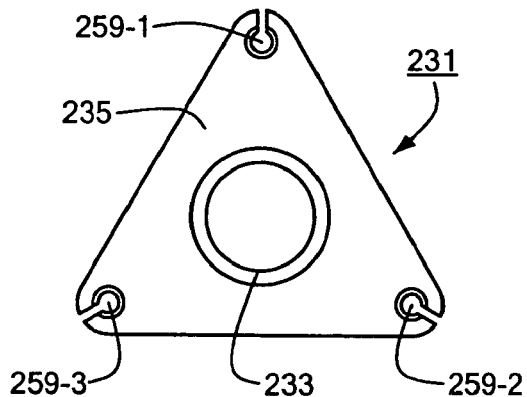
FIGS. 12(a) and 12(b) are proximal and distal views, respectively, of the bolster carrier shown in FIG. 10.
Figure 12B:
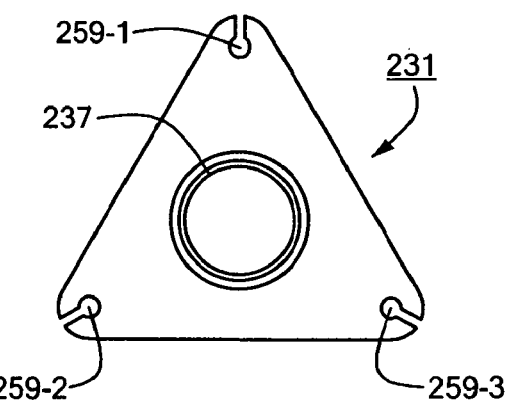

Assembly 211 additionally comprises a bolster carrier 231 (also shown separately in FIGS. 12(a) and 12(b)). Bolster carrier 231 is a generally triangular, unitary member, preferably made of a rigid metal or plastic, and having an annular embossment 233 extending proximally a short distance from its proximal surface 235. Embossment 233 is inserted into the distal end of bore 223 and is secured therewithin. For reasons to become apparent below, embossment 233 is hollow and has an open distal end 237.

Figure 13:
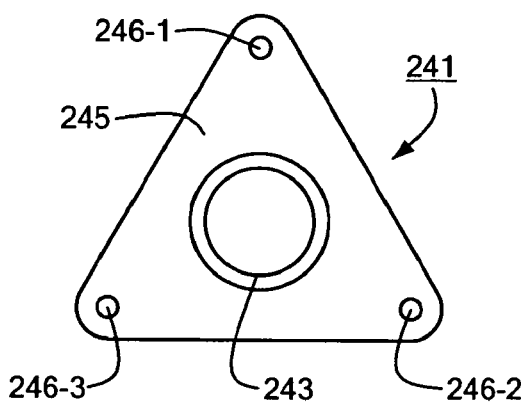
FIG. 13 is a proximal view of the external bolster shown in FIG. 10.

Assembly 211 also comprises an external bolster 241 (also shown separately in FIG. 13), external bolster 241 being a generally triangular, unitary member, preferably made of silicone or a similarly flexible, biocompatible material. Bolster 241 has an outer perimeter dimensioned to approximate the outer perimeter of bolster carrier 231. Bolster 241 is shaped to include an annular embossment 243 extending proximally a short distance from its proximal surface 245, embossment 243 being received in the hollow walls of embossment 233 of bolster carrier 231 through its open distal end 237. Bolster 241 is also shaped to include a plurality of transverse openings 246-1 through 246-3, the purpose of which will be described below.

Figure 14:
FIG. 14 is a side view of one of the needle sheaths shown in FIG. 10.

Assembly 211 further comprises a plurality of identical needle sheaths 251-1, 251-2 and 251-3 (needle sheath 251-1 also being shown separately in FIG. 14). Needle sheaths 251-1 through 251-3 are slotted, tubular members having proximal ends 253-1 through 253-3, respectively, and distal ends 255-1 through 255-3, respectively. Proximal ends 253-1 through 253-3 are fixedly mounted within sleeves 257-1 through 257-3 (sleeve 257-3 not being visible as shown), respectively, formed on proximal portion 219 of barrel portion 217. Distal ends 255-1 through 255-3 are fixedly mounted within slotted openings 259-1 through 259-3 located near the vertices of bolster carrier 231.

Assembly 211 further comprises a plurality of identical needle assemblies 261-1 through 261-3. Needle assemblies 261-1 through 261-3, which may be of the type disclosed in U.S. Pat. Nos. 4,705,040 and 5,341,823 or commercially available as Brown/Mueller T-Fastener/Needle Devices (Boston Scientific Corporation, Watertown, Mass.), are slidably mounted in sheaths 251-1 through 251-3, respectively. (Although not shown, the distal ends of assemblies 261-1 through 261-3 may be covered with removable protective sheaths or the like to prevent accidental needle sticks.) Referring now to FIGS. 10 and 15, assembly 261-1 can be seen to include a needle 263 having a longitudinal bore 264 and a slot 265, slot 265 extending a short distance from the distal end of needle 263 and in communication with bore 264. Assembly 261-1 also includes a plunger 267, plunger 267 being slidably mounted within bore 264. Assembly 261-1 additionally includes a short length of tubing 269 slidably disposed within bore 264 and adapted to be ejected from the distal end of bore 264 by distal movement of plunger 267 relative to needle 263. Assembly 261-1 further includes a suture 271 coupled at one end to the approximate midpoint of tubing 269.

Referring back to FIGS. 10 and 11, assembly 211 further includes a trocar 281, trocar 281 being made of a rigid metal and having a sharp distal end 283 and an enlarged proximal end 285. Trocar 281 is appropriately dimensioned to be slidably and removably mounted in bore 223 of casing 213, with distal end 283 of trocar 281 being positionable past bolster carrier 231 and external bolster 241 to form an incision in a patient.

Assembly 211 further includes a feeding tube assembly 291 (which is also shown separately in FIG. 16), assembly 291 comprising a feeding tube 293 having an internal bolster 294 at its distal end, an inner sheath 295 and an outer sheath 296. Feeding tube 293 and internal bolster 294 may be identical to feeding tube 13 and bolster 14, respectively, of assembly 11. Inner sheath 295 is a unitary, tubular member having a proximal end 297 and a distal end 299. Proximal end 297 of inner sheath 295 is inserted into and secured within a tubular handle 301. Tube 293 is inserted into inner sheath 295, with proximal end 293-1 of tube 293 extending proximally beyond handle 301 and with bolster 294, in a compressed state, positioned just distally of distal end 299 of inner sheath 295 and engageable therewith. For reasons to become apparent below, inner sheath 295 is appropriately dimensioned to permit tube 293 to slide relative thereto. Outer sheath 296 is a unitary, tubular member having a proximal end 305 and a distal end 307. Proximal end 305 of outer sheath 296 is inserted into and secured within a tubular handle 309. For reasons to become apparent below, outer sheath 296 is appropriately dimensioned to receive bolster 294 in a compressed state and to permit inner sheath 295 to slide relative to outer sheath 296. Bolster 294, distal end 299 of inner sheath 295 and distal end 293-2 of tube 293 are all positioned within outer sheath 296. To launch tube 293 and bolster 294 using assembly 291, one slides inner sheath 295 distally relative to outer sheath 296 until inner sheath 295 advances bolster 294 beyond distal end 307 of outer sheath 296, thereby allowing bolster 294 to decompress to its relaxed state. Inner sheath 295 and outer sheath 296 are then withdrawn proximally relative to bolster 294.

To use assembly 211 to fasten together the abdominal and stomach walls of a patient, one positions casing 213 (with bore 223 preferably temporarily unoccupied by either trocar 281 or assembly 291) so that external bolster 241 is placed against the abdominal wall of a patient and centered around a desired incision site. One then sufficiently advances needle assemblies 261-1 through 261-3 in sheaths 251-1 through 251-3, respectively, so that needles 263-1 through 263-3, respectively, perforate the abdominal and stomach walls of the patient. Next, plungers 267 are moved distally to eject tubes 269-1 through 269-3 from needles 263-1 through 263-3, respectively. Needles 263-1 through 263-3 are then withdrawn proximally from the patient and may additionally be proximally withdrawn from sheaths 251-1 through 251-3 to avoid accidental needle sticks. Next, sutures 271-1 through 271-3 are pulled taut and then crimped, knotted, or the like to tack together the abdominal and stomach walls. Because sutures 271-1 through 271-3 extend through openings 246-1 through 246-3, respectively of bolster 241, bolster 241 becomes coupled in this manner to the patient.

It should be noted that, although needle assemblies 261-1 through 261-3 have been described above as being operated simultaneously, they are preferably advanced serially to minimize the possibility of needles 263-1 through 263-3 pushing away the stomach.

As can readily be appreciated, one benefit to using assembly 211 in the above-described manner to fasten together the abdominal and stomach walls is that the spacing and relative positions of the fasteners may be controlled according to a predetermined design.

Once the abdominal and stomach walls have been fastened to one another in the above manner, one may use trocar 281 to form incisions in the abdominal and stomach walls, respectively, of the patient. This may be done by inserting distal end 283 of trocar 281 into bore 223 and advancing trocar 281 distally until proximal end 285 of trocar 281 abuts casing 213, at which time distal end 283 will have extended distally beyond bolster 241 and entered the patient.

Trocar 281 may then be removed from bore 223, and assembly 291 may be inserted into bore 223. Assembly 291 may then be used to launch tube 293 and bolster 294 in the manner discussed above.

It should be noted that, instead of using a feeding tube having a self-expandable, mushroom-shaped or dome-shaped bolster like bolster 294, one could use a feeding tube having an inflatable balloon-type bolster or any other bolster that is transformable between an expanded anchoring state and a collapsed state.

It should also be noted that, although assembly 211 has been described herein in the context of gastrostomy feeding, assembly 211 is not limited to gastrostomy feeding and may be used for other types of feeding, as well as for drainage.

The embodiments of the present invention described above are intended to be merely exemplary and those skilled in the art shall be able to make numerous variations and modifications to it without departing front the spirit of the present invention. For example, it is to be understood that other types of anchoring mechanisms, other than those disclosed, can be used and that other types of sutures and threads can also be used. All such variations and modifications are intended to be within the scope of the present invention as defined in the appended claims.

What is claimed is:

1. A medical catheter implanting assembly comprising:
   a casing comprising a proximal portion, a distal portion, and a longitudinal bore extending entirely therethrough;
   a bolster carrier having an embossment, said embossment being received within a distal end of the longitudinal bore;
   a plurality of needle sheaths; and
   an external bolster having a plurality of transverse openings.

2. The medical catheter implanting assembly of claim 1, wherein the casing is gun-shaped and comprises a handle portion and barrel portion.

3. The medical catheter implanting assembly of claim 1, wherein the bolster carrier is a substantially triangular-shaped unitary member.

4. The medical catheter implanting assembly of claim 2, wherein the casing further comprises:
   a plurality of sleeves mounted on a proximal portion of the barrel portion, each sleeve for receiving a proximal end of one of the plurality of needle sheaths.

5. The medical catheter implanting assembly of claim 1, wherein the bolster carrier further comprises:
   a plurality of slotted openings, each slotted opening for receiving a distal end of one of the plurality of needle sheaths.

6. The medical catheter implanting assembly of claim 1, said embossment having a longitudinal opening extending therethrough.

7. The medical catheter implanting assembly of claim 1, further comprising:
   a trocar having a sharp distal end, said trocar dimensioned to be slidably and removably received within the longitudinal bore of the casing, said sharp distal end being positionable distal to the external bolster and the bolster carrier.

8. The medical catheter implanting assembly of claim 1, further comprising:
   a feeding tube assembly dimensioned to be slidably and removably received within the longitudinal bore of the casing.

9. The medical catheter implanting assembly of claim 8, wherein said feeding tube assembly comprises:
   an outer sheath having a proximal end and a distal end;
   an inner sheath having a proximal end and a distal end, said inner sheath being slidably mounted within said outer sheath; and
   a medical catheter having an internal bolster at a distal end thereof, said medical catheter being inserted into the inner sheath, and said internal bolster being retained in a compressed state by the outer sheath.

10. The medical catheter implanting assembly of claim 1, further comprising:
    a plurality of needle assemblies slidably mounted in the plurality of needle sheaths.

11. The medical catheter implanting assembly of claim 10, wherein each of the plurality of needle assemblies comprises:
    a needle having a longitudinal bore and a slot near the distal end of the needle, said slot in communication with the longitudinal bore;
    a plunger slidably mounted in the longitudinal bore;
    a length of tubing mounted in the slot; and
    a suture coupled to the length of tubing.

12. The medical catheter implanting assembly of claim 11, wherein a distal end of the suture is coupled to the approximate midpoint of the length of tubing.

13. The medical catheter implanting assembly of claim 12, wherein the length of tubing is adapted to be ejected from the distal end of the slot by distal movement of the plunger.

14. A method of anchoring a patient's abdominal wall and stomach wall together comprising:
    (a) using a medical catheter implanting assembly to align a plurality of needle assemblies, each needle assembly comprising:
        a needle having a longitudinal bore and a slot near the distal end of the needle, said slot in communication with the longitudinal bore;
        a plunger slidably mounted in the longitudinal bore;
        a length of tubing mounted in the slot; and
        a suture coupled to the length of tubing;
    (b) extending the needle through the stomach wall and the abdominal wall of the patient;
    (c) advancing the plunger distally to eject the length of tubing from the slot;
    (d) retracting the needle and plunger from the patient; and
    (e) pulling the suture taut to anchor the abdominal wall and the stomach wall together.

15. The method of claim 14, further comprising:
performing the steps (b) through (e) for each needle assembly sequentially.

16. The method of claim 14, wherein the medical catheter implanting assembly comprises:
a casing comprising a proximal portion, a distal portion, and a longitudinal bore extending entirely therethrough;
a bolster carrier having an embossment, said embossment being received within a distal end of the longitudinal bore;
a plurality of needle sheaths; and
an external bolster having a plurality of transverse openings,
the method further comprising:
inserting each needle assembly through one of said plurality of needle sheaths and through one of the plurality of transverse openings of the external bolster.

17. The method of claim 16, further comprising:
inserting a trocar into the longitudinal bore of the casing, said trocar having a pointed distal end;
puncturing the patient's stomach with the pointed distal end of the trocar;
removing the trocar from the longitudinal bore; and
inserting a feeding tube assembly through the longitudinal bore into the patient's stomach.

18. The method of claim 17, wherein said feeding tube assembly comprises:
an outer sheath having a proximal end and a distal end;
an inner sheath having a proximal end and a distal end, said inner sheath being slidably mounted within said outer sheath; and
a medical catheter, having an internal bolster at a distal end thereof, said medical catheter being inserted into the inner sheath, and said internal bolster being retained in a compressed state by the outer sheath,
the method further comprising:
sliding the inner sheath distally relative to the outer sheath such that the internal bolster is advanced beyond the distal end of the outer sheath;
expanding the internal bolster; and
retracting the inner sheath and the outer sheath from the patient.

19. A method of inserting a feeding tube into a patient comprising:
using a medical catheter implanting assembly comprising:
a casing comprising a proximal portion, a distal portion, and a longitudinal bore extending entirely therethrough;
a bolster carrier having an embossment, said embossment being received within a distal end of the longitudinal bore;
a plurality of needle sheaths; and
an external bolster having a plurality of transverse openings;
inserting a trocar into the longitudinal bore of the casing, said trocar having a pointed distal end;
puncturing the patient's stomach with the pointed distal end of the trocar;
removing the trocar from the longitudinal bore; and
inserting a feeding tube assembly through the longitudinal bore into the patient's stomach.

20. The method of claim 19, wherein said feeding tube assembly comprises:
an outer sheath having a proximal end and a distal end;
an inner sheath having a proximal end and a distal end, said inner sheath being slidably mounted within said outer sheath; and
a medical catheter, having an internal bolster at a distal end thereof, said medical catheter being inserted into the inner sheath, and said internal bolster being retained in a compressed state by the outer sheath,
the method further comprising:
sliding the inner sheath distally relative to the outer sheath such that the internal bolster is advanced beyond the distal end of the outer sheath;
expanding the internal bolster; and
retracting the inner sheath and the outer sheath from the patient.

* * * * *